United States Patent [19]

DeVoe et al.

[11] Patent Number: 4,585,559

[45] Date of Patent: Apr. 29, 1986

[54] INSOLUBLE CHELATING COMPOSITIONS

[75] Inventors: Irving W. DeVoe, Baie d'Urfe; Bruce E. Holbein, Pointe-Claire, both of Canada

[73] Assignee: DeVoe-Holbein International, N.V., Curacao, Netherlands Antilles

[21] Appl. No.: 625,539

[22] Filed: Jun. 28, 1984

Related U.S. Application Data

[60] Division of Ser. No. 469,431, Feb. 24, 1983, Pat. No. 4,530,963, which is a continuation-in-part of Ser. No. 417,376, Sep. 13, 1982, abandoned.

[30] Foreign Application Priority Data

Aug. 20, 1982 [CA] Canada .................................. 409869
Jan. 31, 1983 [CA] Canada .................................. 420567

[51] Int. Cl.$^4$ ............................................. B01D 15/00
[52] U.S. Cl. .................................... 210/679; 210/682; 210/688
[58] Field of Search ...................... 210/682, 679, 688; 423/6

[56] References Cited

U.S. PATENT DOCUMENTS

| | | | |
|---|---|---|---|
| 2,815,329 | 12/1957 | Germain | 252/179 |
| 2,847,308 | 8/1958 | Bersworth et al. | 99/48 |
| 3,118,823 | 1/1964 | Gaeumann et al. | 195/80 |
| 3,153,621 | 10/1964 | Gaeumann et al. | 195/80 |
| 3,320,033 | 5/1967 | Coren | 23/337 |
| 3,390,161 | 6/1968 | Fraioli | 260/439 |
| 3,519,538 | 7/1970 | Messing et al. | 195/63 |
| 3,556,945 | 1/1971 | Messing et al. | 195/63 |
| 3,652,761 | 4/1972 | Weetall | 424/12 |
| 3,715,278 | 2/1973 | Miller | 195/63 |
| 3,755,161 | 8/1973 | Yokota et al. | 210/679 |
| 3,886,080 | 5/1975 | Schucker et al. | 252/176 |
| 3,896,045 | 7/1975 | Peeters et al. | 423/2 |
| 3,904,373 | 9/1975 | Harper | 252/408 |
| 3,954,936 | 5/1976 | Sherda | 423/24 |
| 3,970,553 | 7/1976 | Terajima et al. | 210/688 |
| 4,033,764 | 7/1977 | Colegate et al. | 423/24 |
| 4,034,139 | 7/1977 | Mazarguil et al. | 428/405 |
| 4,152,493 | 5/1979 | Yotsumoto et al. | 210/688 |
| 4,174,319 | 11/1979 | Kobuke | 260/239 BC |
| 4,203,952 | 5/1980 | Hancock | 423/6 |
| 4,230,803 | 10/1980 | Weidenbach et al. | 435/176 |
| 4,284,512 | 8/1981 | Hodgkin | 210/688 |
| 4,290,892 | 9/1981 | Abbott | 210/656 |
| 4,414,183 | 11/1983 | Sasaki et al. | 210/688 |

FOREIGN PATENT DOCUMENTS

| | | |
|---|---|---|
| 648981 | 9/1962 | Canada . |
| 664441 | 6/1963 | Canada . |
| 715051 | 8/1965 | Canada . |
| 742670 | 9/1966 | Canada . |
| 773540 | 12/1967 | Canada . |
| 775539 | 1/1968 | Canada . |
| 876754 | 7/1971 | Canada . |
| 879738 | 8/1971 | Canada . |
| 919707 | 1/1973 | Canada . |
| 951329 | 7/1974 | Canada . |
| 790626 | 9/1975 | Canada . |
| 800902 | 11/1976 | Canada . |
| 811124 | 11/1976 | Canada . |
| 1054081 | 8/1978 | Canada . |
| 821214 | 12/1979 | Canada . |
| 1102346 | 6/1981 | Canada . |
| 1102347 | 6/1981 | Canada . |
| 1103035 | 8/1982 | Canada . |
| 1129188 | 8/1982 | Canada . |

OTHER PUBLICATIONS

Chemical Abstracts, vol. 88 (Abstract No. 137239w).
Barnes and Genna (Anal. Chem., 1979).
Colella et al., (Anal. Chem., 1980: 967–72; 2347–350).
(List continued on next page.)

Primary Examiner—Ivars Cintins
Attorney, Agent, or Firm—Schwartz, Jeffery, Schwaab, Mack, Blumenthal & Evans

[57] ABSTRACT

The present invention relates to insoluble compositions, which are capable of removing metal (e.g. selectively) from solution (e.g. $Fe^{3+}$ from a liquid nutrient medium so as to lower the $Fe^{3+}$ content to less than 0.1 µM); the insoluble compositions comprise: a suitable insoluble carrier and organic co-ordinating sites covalently fixed to the surface of said carrier, said co-ordinating sites being capable of chelating $Fe^{3+}$, $Th^{4+}$ and/or $UO_2^{2+}$.

38 Claims, 3 Drawing Figures

OTHER PUBLICATIONS

Neilands et al., (*J. Bio. Chem.*, 1981).
Messer et al., (*J. Nutr.*, 1982).
Judgement (Annex A) and a ruling on motion (Annex B) rendered by a Justice of the Superior Court, District Montreal, Quebec, Canada.
*Chemical Abstracts*, vol. 82 (Abstract No. 18076g).
*Chemical Abstracts*, vol. 81 (Abstract No. 106615s.
*Chemical Abstracts*, vol. 80 (Abstract No. 30457y).
J. Bacteriology 149: 880, 1982.
Ann. Rev. Biochem. 50: 715–731, 1981.
Amer. Chem. Soc. 32: 183–190, 1979.
Inman, in Methods of Enzymology, XXXIV B:30 (Jakoby W. B. Ed.), Academic Press, New York (1974).
Archibald and DeVoe 1980, "Iron Acquisition by Neisseria Meningitidies in Vitro," Infect. Immun. 27: 322–334.
Weetall and Filbert, Methods of Enzymology XXXIV B: 59–72, 1974.
Biochemistry 8:4074 (1969).

\* – A, C AND E IRON LOADED COMPOSITION
\*¹ – B AND D REGENERATED COMPOSITION

INSOLUBLE CHELATING COMPOSITIONS

This is a division of application Ser. No. 469,431, filed Feb. 24, 1983, U.S. Pat. No. 4,530,963, which is a continuation-in-part of application Ser. No. 417,376, filed Sept. 13, 1982, and now abandoned.

The present invention relates to a composition useful for the removal of metals, in particular iron, from liquid media. The composition, can for example, be used to lower the iron concentration of a liquid medium to less than 0.1 μM.

BACKGROUND OF THE INVENTION

Iron is an essential nutrient for all living things; a large number of cellular enzymes and other proteins require iron in order to function properly. Although iron is amongst the most plentiful of metals, it is difficult for biological systems to acquire; in aerobic environments of substantially neutral pH, iron exists as its oxidized $Fe^{3+}$ form which readily hydrates to highly insoluble $Fe(OH)_3$ polymeric forms. To ensure accessability of iron in their environment, aerobic and facultative micro-organisms synthesize and release into their environment highly selective iron chelating agents called siderophores, the function of which is to provide the microbes with this vital nutrient. The siderophores released by the microbes solubilize iron, putting it into a form readily usable by them. Thus, a free, microbial siderophore is a growth promoting substance for those organisms which can utilise the particular siderophore in question.

SUMMARY OF THE INVENTION

In accordance with the present invention it has been determined that removal of iron (e.g. $Fe^{3+}$) from a liquid nutrient medium will substantially restrict the proliferation of microbes provided that the residual iron concentration in the medium is below 0.1 μM; and this notwithstanding that the other required nutrients may be present in amounts sufficient for the support of microbial growth.

Thus, it is advantageous to have compositons able to remove iron from a liquid, nutrient medium since the absence or limited presence of iron will inhibit microbial growth in such a medium. For example, the specific removal of iron from an ophthalmic solution will inhibit microbial growth and spoilage of such a solution. The removal of iron from such a solution would obviate the addition of conventional microbial growth inhibitors which can create their own problems such as toxicity, etc.

Removal of iron from liquid media prior to the present invention did present problems (see Neilands, J. Bacteriology 149: 880, 1982). Commercially available products (e.g. Chelex 100 sold by BioRad) have a low selectivity for iron. Additionally, other important cations ($Mn^{2+}$, $Mg^{2+}$) removed by such commercial products are often desirable components of a liquid medium. Commercial ion exchange products can also liberate sodium or potassium ions into the liquid medium being treated which may not be desirable.

Thus, it would be advantageous to be able to remove iron from solution while at the same time avoiding liberating into the solution undesirable ions.

In general, it would be advantageous to be able to remove iron from solution when the presence of iron is undesirable, e.g. when iron is considered a contaminant at concentrations greater than 0.1 μM.

Free microbial siderophores cannot be used to remove iron from a liquid medium; the natural purpose of such siderophores is to make iron soluble and available to microorganisms. The addition of free siderophores to a liquid medium would therefore enhance the growth of microorganisms which could utilize iron solubilized thereby. Additionally it would be extremely difficult at the very least, to recover such siderophores loaded with iron.

Nevertheless, it would be advantageous to be able to make use of properties of siderophoric compounds such as microbial siderophores and other organic compounds which can provide co-ordinating groups or ligands for the chelating of iron (i.e. $Fe^{3+}$).

In accordance with the present invention, it has also been determined that microbial siderophores and other organic compounds possessing the same or similar co-ordinating groups or ligands can, in addition to $Fe^{3+}$, remove $Th^{4+}$ and $UO_2^{2+}$ from solution. If desired, it is also possible to separate $Th^{4+}$ from $UO_2^{2+}$ if their ions are present in solution in combination.

The present invention in general relates to insoluble compositions, which are capable of removing metal (e.g. selectively) from solution (e.g. $Fe^{3+}$ from a liquid nutrient medium so as to lower the $Fe^{3+}$ content to less than 0.1 μM); the insoluble compositions comprise:
(i) a suitable insoluble carrier and
(ii) organic co-ordinating sites covalently fixed to the surface of said carrier
said co-ordinating sites being capable of chelating $Fe^{3+}$, $Th^{4+}$ and/or $UO_2^{2+}$.

In accordance with the present invention the necessary co-ordinating sites may, for example, be provided by fixing an organic chelating compound such as a microbial siderophore to a suitable carrier (infra).

Thus in accordance with one aspect of the present invention, there is, in particular, provided a method for inhibiting microbial growth in a liquid nutrient medium containing $Fe^{3+}$ by lowering the $Fe^{3+}$ content thereof to less than 0.1 μM characterized in that said medium is contacted with an insoluble siderophoric composition and thereafter said insoluble siderophoric composition loaded with $Fe^{3+}$ is separated from said medium, said insoluble siderophoric composition comprising:
(1) one or more organic siderophoric compounds, covalently fixed to the surface of
(2) a suitable insoluble carrier, said organic siderophoric compounds possessing one or more co-ordinating sites capable of chelating $Fe^{3+}$.

DETAILED DESCRIPTION OF THE PREFERRED EMBODIMENTS

Figure 1:
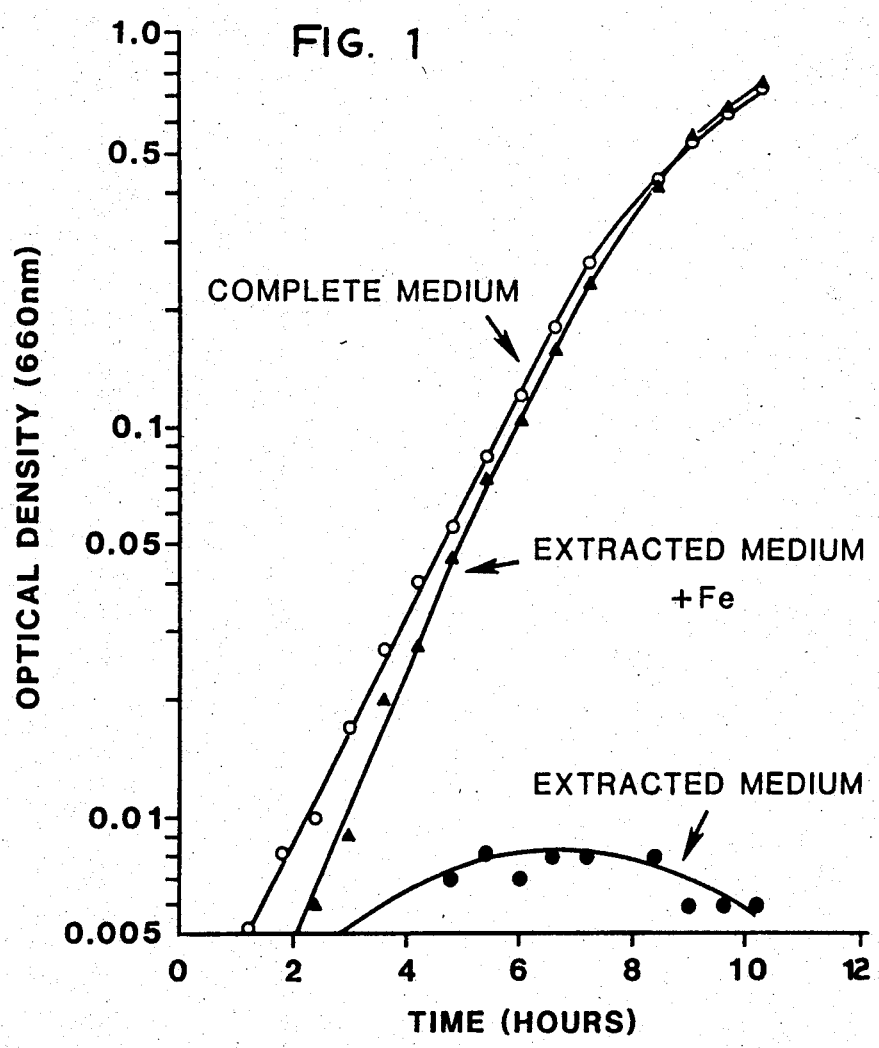

An insoluble siderophoric composition, for the purposes of this aspect of the invention, is a composition having a chelating activity with respect to iron, and in particular a selective chelating activity.

The organic co-ordinating sites of suitable organic siderophoric compounds may, for example, be provided by groups selected from the class consisting of
(a) N-substituted hydroxamate groups of formula

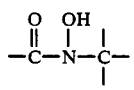

(b) phenolate groups of formula

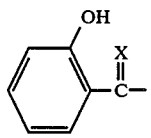

X being an atom of O or N—
(c) catecholate groups of formula

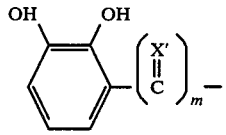

X' being an atom of O or N— and m being 0 or 1, and
(d) mixtures of two or more of the above groups; see below.

If desired, a catechol (1,2 dihydroxybenzene) compound, as defined hereinafter may be used as a siderophoric compound to provide catecholate type co-ordinating sites.

The insoluble siderophoric composition can for example be used to specifically remove iron from liquid media such as water, juices, wine, beer, cider, chemical solutions, microbial and tissue culture media, pharmaceutical media, etc.

In accordance with another aspect of the present invention there is provided an insoluble composition comprising a member selected from the class consisting of
(A) an insoluble composition comprising
  (1) one or more organic chelating compounds, covalently fixed to the surface of
  (2) a suitable insoluble carrier,
  said organic chelating compounds possessing one or more co-ordinating sites, said organic chelating compounds being selected from the class consisting of microbial siderophores and
(B) an insoluble composition comprising
  (1) one or more catechol compounds covalently fixed to the surface of
  (2) a suitable insoluble carrier,
  said catechol compounds being covalently fixed to the surface of said carrier at the benzene ring thereof, said catechol compounds being selected from the group consisting of unsubstituted catechol and catechol substituted on the benzene ring by one or two electrophilic substituents.

The above compositions, in accordance with this other aspect of the present invention can be used to remove $Fe^{3+}$, $Th^{4+}$, $UO_2^{2+}$ and mixtures thereof from solution.

Thus this other aspect of the present invention also provides a method for removing $Fe^{3+}$, $Th^{4+}$, $UO_2^{2+}$ and mixtures thereof from solution characterized in that the solution is contacted with an insoluble composition as defined above. Thereafter, the composition loaded with metal may be separated from the treated solution. For example, the iron content of a liquid medium amy in this way be lowered to less than 0.1 $\mu M$. Thus an insoluble composition in accordance with this aspect of the present invention may advantageously be used as a siderophoric composition to remove $Fe^{3+}$ from liquid nutrient medium.

In particular, this aspect of the present invention also provides a method for inhibiting microbial growth in a liquid nutrient medium containing $Fe^{3+}$, by lowering the $Fe^{3+}$ content thereof to less than 0.1 $\mu M$ characterized in that said medium is contacted with an insoluble composition as defined above and thereafter said composition loaded with $Fe^{3+}$ is separated from the medium. The iron loaded composition can, for example be recovered by filtration.

Compositions as defined above, loaded with $Fe^{3+}$, $Th^{4+}$ or $UO_2^{2+}$, may possibly be regenerated by chemical means suitable for the removal of the chelated metal; the so regenerated composition can thereafter be recycled for further use.

The insoluble compositions referred to above have a very high affinity for $Th^{4+}$ and $UO_2^{2+}$. They can be used to remove $Th^{4+}$ and $UO_2^{2+}$ from solution even if present in trace amounts, e.g. to obtain solutions containing <0.2 nM of these ions.

The present invention thus provides not only a mechanism for the removal of $Fe^{3+}$, $Th^{4+}$ and $UO_2^{2+}$, from liquid media but also for the preservation of various liquid media through the removal of iron therefrom, i.e. rendering liquid nutrient media highly resistant to microbial growth since any microorganism present cannot proliferate due to the insufficient amount of iron present.

In accordance with a further aspect of the present invention there is provided a method for treating a composition loaded with $Th^{4+}$ and $UO_2^{2+}$ to separate $Th^{4+}$ therefrom, characterized in that said composition is contacted with an aqueous solution containing a suitable $Th^{4+}$ chelating agent and an organic acid, said organic acid being a carboxylic acid, said solution having a pH greater than 2, said composition comprising a member selected from the class consisting of
(A) an insoluble composition comprising
  (1) one or more organic chelating compounds covalently fixed to the surface of
  (2) a suitable insoluble carrier,
  said organic chelating compounds possessing one or more co-ordinating sites, said organic chelating compounds being selected from the class consisting of microbial siderophores, and
(B) an insoluble composition comprising
  (1) one or more catechol compounds covalently fixed to the surface of
  (2) a suitable insoluble carrier,
  said catechol compounds being covalently fixed to the surface of said carrier at the benzene ring thereof, said catechol compounds being selected from the group consisting of unsubstituted catechol and catechol substituted on the benzene ring by one or two electrophilic substituents.

In accordance with this further aspect of the present invention, it is possible to separate $Th^{4+}$ and $UO_2^{2+}$ which are present in a solution. Thus, for example, an aqueous solution containing $Th^{4+}$ and $UO_2^{2+}$ and having a pH of about 7 can be contacted with an insoluble composition as defined above, (preferably a composition incorporating a catechol compound fixed to a silica based carrier), to give rise to a composition loaded with $Th^{4+}$ and $UO_2^{2+}$. This loaded composition can then be recovered and treated, as outlined above to separate the $Th^{4+}$ from the composition, to provide a treated composition loaded with $UO_2^{2+}$ but having a substantially reduced $Th^{4+}$ content. The treated composition can then be contacted with, for example, an aqueous acidic solution to recover a concentrated $UO_2^{2+}$ solution; for example a composition incorporating a catechol compound fixed to a silica based carrier can be treated with an aqueous mineral acid (e.g. HCl) having a $pH \approx 0.8–1.5$ to recover a concentrated $UO_2^{2+}$ solution.

The $Th^{4+}$ and $UO_2^{2+}$ solution can for example, be provided by treating in a known manner, radioactive materials from atomic reactors. For example, Th can be converted to U by treating solid $^{232}Th$ with neutrons which convert $^{232}Th$ to $^{233}Th$. The $^{233}Th$ decays to a fissionable type of uranium i.e. $^{233}U$. The mixture of these metals can then be solubilized with a suitable agent such as $HNO_3$. The obtained solution, once neutralized to a $pH > 4$ can then be treated for the separation of the metals as outlined above, i.e. to produced a concentrated solution of the fissionable type of uranium.

Organic chelating compounds, e.g. sidephoric compounds, useful in accordance with the present invention may also form complexes with certain other transition, rare earths and actinide metals due to the structural (atomic) similarities with iron; however, the complexes are formed at lower affinities than, for example $UO_2^{2+}$ or iron. Although the compositions of the present invention can possibly be used for the removal of these other metals from liquid media, the following discussion will be directed to the removal of $Fe^{3+}$, $Th^{4+}$ and $UO_2^{2+}$ from liquid media.

In accordance with the present invention, a general process for the preparation of an insoluble composition as defined above can be characterized in that organic co-ordinating sites capable of chelating metal are covalently fixed to the surface of a suitable carrier. Any suitable means of covalently fixing organic co-ordinating sites to a carrier can be used provided that the composition obtained has the necessary chelating activity.

If it is desired to produce a siderophoric composition comprising one or more organic siderophoric compounds fixed to a suitable carrier then the process of its preparation may be characterized in that a suitable carrier is reacted with one or more organic siderophoric compounds possessing co-ordinating sites capable of chelating $Fe^{3+}$ so as to covalently bond said siderophoric compounds to the surface of said carrier, while maintaining the $Fe^{3+}$ chelating activity of said siderophoric compounds.

The siderophoric compounds as indicated above can be microbial siderophores. In this particular case, the process of preparation can be characterized in that a suitable carrier is reacted with one or more microbial siderophores so as to bond said microbial siderophores to the surface of said carrier, said carrier and said microbial siderophores possessing functional groups reactive one with the other so as to covalently bond said microbial siderophores to said carrier while maintaining the $Fe^{3+}$ chelating activity of said microbial siderophores.

Turning now to the chelating compounds, sufficient metal coordination sites to chelate the metal ions (i.e. $Fe^{3+}$, $Th^{4+}$ and $UO_2^{2+}$) may be provided by a single organic chelating (e.g. siderophoric) compound or alternatively by two or more such compounds; the number of compounds participating in the chelation of the metal ions being dependent upon the number of coordinating sites which are available from a particular compound fixed to a carrier.

The organic chelating compound used can as indicated above be a microbial siderophore. A microbial siderophore may have a molecular weight of less than 2500 Daltons, e.g. a molecular weight in the range of 500 to 2500 Daltons. A microbial siderophore useful in accordance with the present invention can also possess one or more types of metal coordinating sites within its structure. The sites can be provided by groups selected from the class of groups referred to earlier, e.g. N-substituted hydroxamate groups, catecholate groups etc. Siderophores possessing these groups display high selectivity and very high affinities for $Fe^{3+}$, $Th^{4+}$ and $UO_2^{2+}$.

A representative list of microorganisms and their siderophores is given in following table 1:

TABLE 1

| ORGANISM NAME | COMMON NAMES OF SIDEROPHORE OBTAINED THEREFROM |
|---|---|
| Prokaryotes | |
| Enteric species | Enterobactin (enterochelin), Aerobactin |
| *Agrobacterium tumefaciens* | Agrobactin |
| Pseudomonas species | Pyochelin, Pyoverdine, Pseudobactins, Ferribactin |
| *Bacillus megaterium* | Schizokinen |
| Anaboena species | Schizokinen |
| Arthrobacter species | Arthrobactin |
| *Azotobacter vinelandii* | α,ε-bis-2,3,-dihydroxybenzoyllysine |
| Actinomyces species | Ferrioxamines |
| Mycobacterium species | Mycobactins |
| Eukaryotes (Fungi) | Ferrichromes, Copragen |
| Pencillium species, | |
| Aspergillus species, | |
| Neurospora, Ustillago | |
| Rhodotorula species | Rhodotorulic acids |
| Ectomycorrhizal species | Hydroxamate type |

The basic chemical structure, trivial names and possible sources of some types of microbial siderophores are listed below; the term microbial siderophore of course includes any suitable functional derivatives, analogs or enantioforms of these molecules:

(a) Ferrioxamine

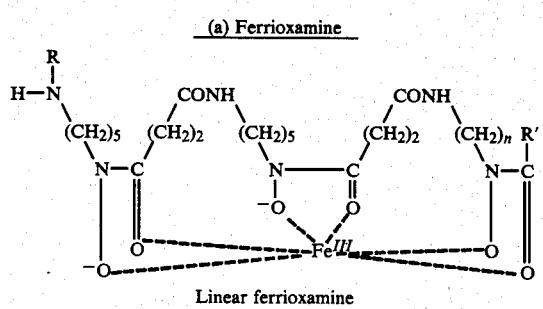

Linear ferrioxamine

-continued
(a) Ferrioxamine

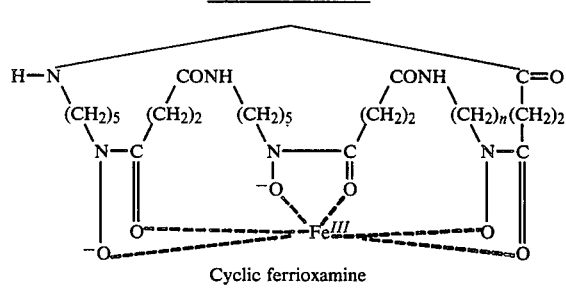

Cyclic ferrioxamine wherein:
R=H or —COCH$_3$; R'=CH$_3$— or HOOC—(CH$_2$)$_2$—; n=4 or 5.

For ferrioxamine B, R=H and R'=CH$_3$—. The mesylate salt of deferrioxamine is marketed by Ciba-Geigy as Desferal (U.S. Pat. Nos. 1964 3,118,823 and 3,153,621; Can. Pat. Nos. 1962 648981 and 715051.

(b) Ferrichromes

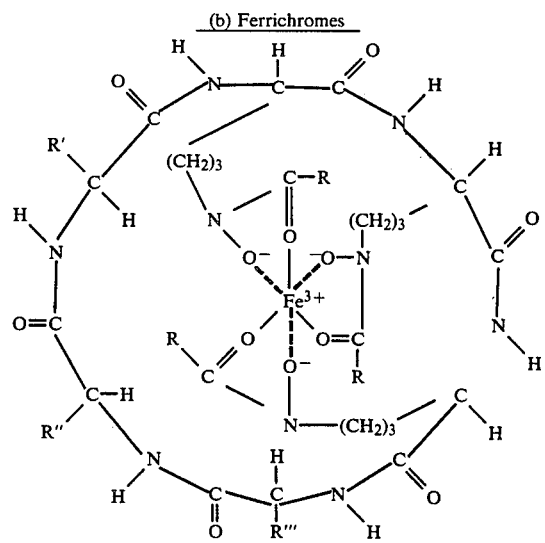

wherein:
R', R", R'''=H
R=—CH$_3$
Ferrichrome
(prototype)

(c) Citrate Hydroxamate Derivatives

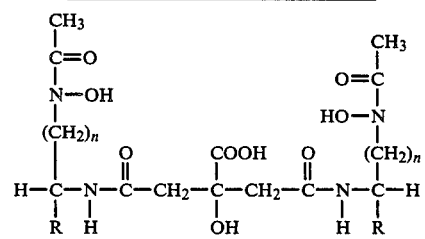

wherein for:

|  | R | n |
| --- | --- | --- |
| schizokinen | H | 2 |
| aerobactin | COOH | 4 |
| arthrobactin | H | 4 |

(d) Rhodotorulic Acids

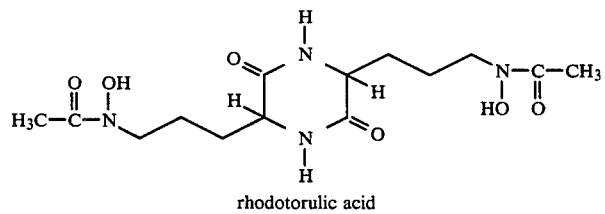

rhodotorulic acid

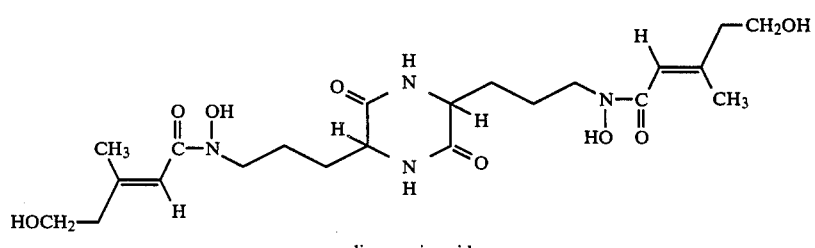

dimerumic acid

-continued
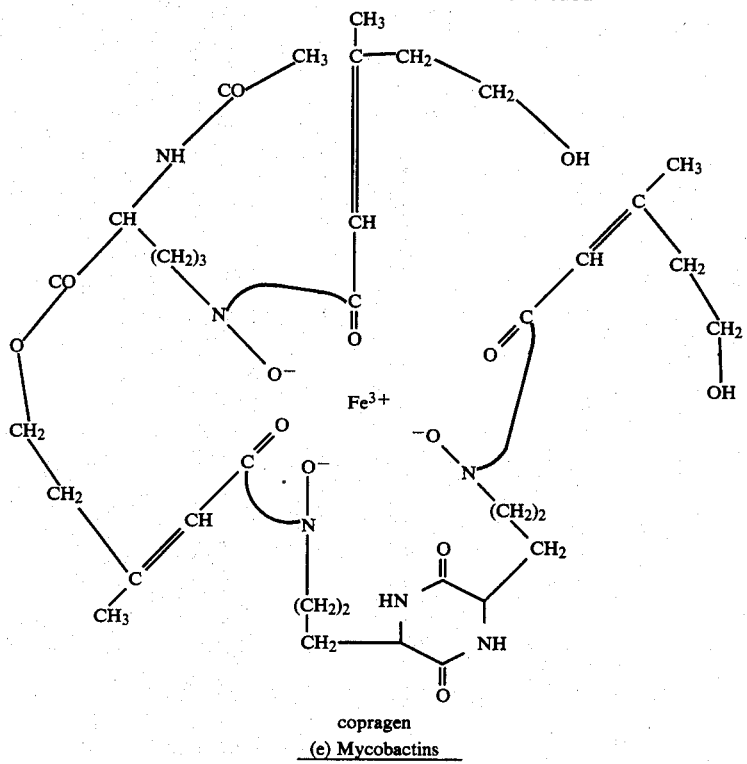
copragen
(e) Mycobactins
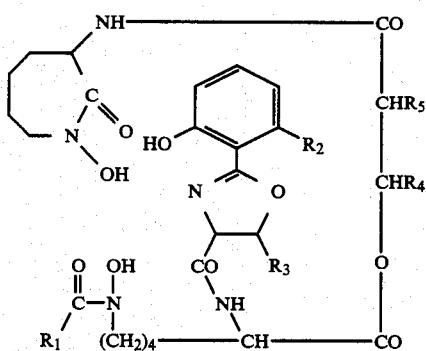
wherein:
 $R_1$ = methyl, ethyl or alkyl or alkenyl of 11 to 20 carbon atoms
 $R_2$ = H or methyl
 $R_3$ = H or methyl
 $R_4$ = methyl, ethyl, or alkyl of 15 to 18 carbon atoms
 $R_5$ = H or methyl
(f) Fusarinines
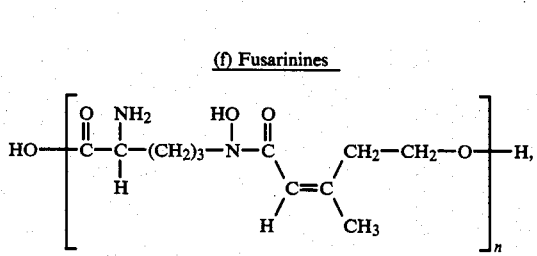
wherein: n = 1 to 3
(g) Enterobactin -continued
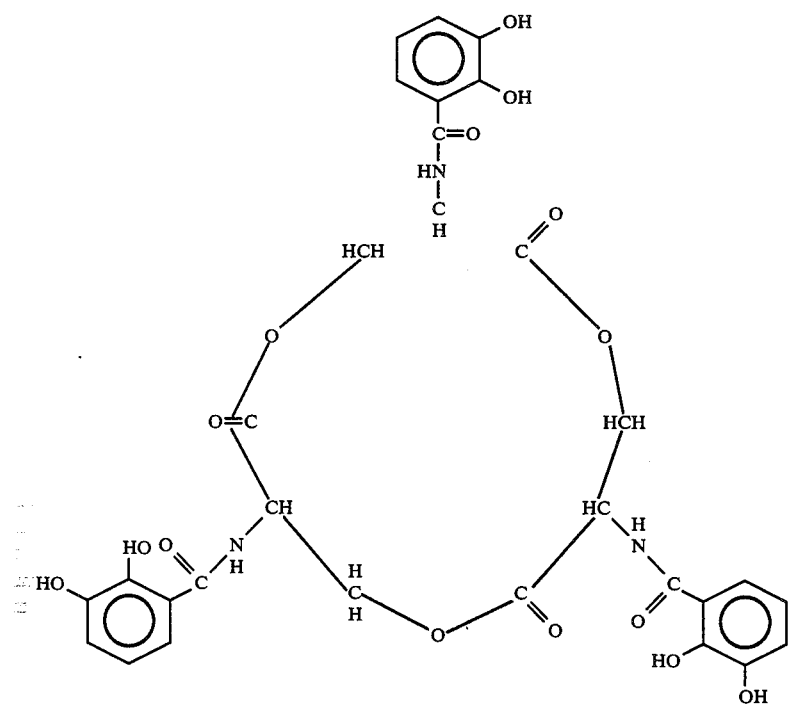
(h) Agrobactins
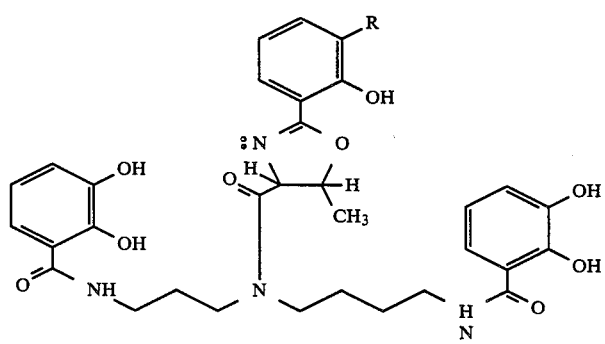
60
wherein:
R=H,OH (i) Pseudobactin

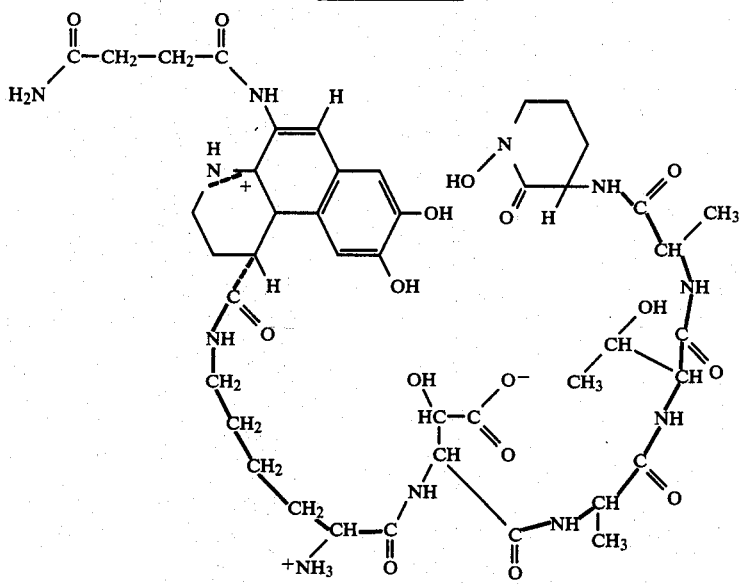

A detailed description of the above siderophores is given by Neilands (Annu. Rev. Biochem. 50: 715-731, 1981), and their coordination chemistry has been reviewed by Raymond and Carrano (*Accounts of Chemical Research*, Vol. 12, No. 5 (1979), at pages 183-190).

Microbial siderophores can be extracted for example from spent microbial culture media with organic solvents. Examples of such methods are given in U.S. Pat. Nos. 3,118,823 and 3,153,621 as well as Canadian Pat. Nos. 648,981 and 715,051. For example, siderophores possessing hydroxamate ligands may be obtained in this fashion. Hydroxamate microbial siderophores are distributed widely throughout the prokaryotic and eukaryotic microbial world, but to date, only bacteria are known which produce typical mono- and dihydroxybenzoic acid-bearing siderophores.

Some microbial siderophores, their analogs and/or their enantioforms have been chemically synthesized in the laboratory:

(i) enterobactin, its enantioform and carboxylic, methyl, and aromatic analogs;
(ii) $N^1$, $N^8$-bis-2,3-dihydroxybenzoylspermidine;
(iii) ferrichrome and enantio-ferrichrome.

Other processes for the preparation of various siderophores are described in Canadian Pat. Nos. 742,670, 746,873, 773,540 and 775,539.

A discussion of the preparation of siderophores by denovo synthesis can be found in Neilands Review 1981 and Neilands et al J. Biol. Chem. 256; 3831-3238, 1981.

The ferrioxamine B is sold commercially under the designation Desferal which is a trademark of Ciba-Geigy.

The microbial siderophores, ferrioxamine and enterobactin, referred to above are prototypical natural microbial siderophores and each represents the general structure and properties of hydroxamate and catecholate-bearing siderophores respectively. These particular siderophores will be referred to below (e.g. in the examples). For the purposes of this specification the expression des as it appears before ferrioxamine etc is to be understood to refer to ferrioxamine etc wherein coordinating sites are unoccupied e.g. they are not iron loaded.

Turning now to carriers suitable in accordance with the present invention, they must of course be insoluble in the liquid medium of intended use; for example, the carrier can be water insoluble. Desirably, the carrier is also inert in the liquid medium of intended use. The carriers can be in particulate or solid form.

The carrier can be an organic or inorganic compound. For example, the carrier may be a natural or modified natural polymer (e.g. lignin, agar, alignate, glucan, cellulose, dextran, cellulose acetate, humic acid, etc.) a synthetic organic polymer (e.g. a polyamide, a polyamine, a polyacrylamide, a polyester, a polyurethane, a polyethylene, a polystyrene, a polypropylene, a polycarbonate, a silicone, nylon, latex, a polyfluroolefin, etc.) or an inorganic material (a ceramic, a glass, carbon, etc.).

As indicated above the present invention provides a (siderophoric) composition comprising one or more microbial siderophores which are covalently immobilized or fixed on a suitable insoluble carrier in such a way that the microbial siderophores retain their high chelating affinity for metal ions, i.e. iron.

A number of known processes are suitable for the binding of microbial siderophores to carriers so as to preserve the iron chelating or complexing properties thereof. For example, the commonly used methods for covalently binding enzymes to insoluble carriers can be adapted for the immobilization of microbial siderophores. See, for example <<Methods of Enzymology>>, XXXIV B:30 (Jakoby W. B. Ed.) Academic Press, New York (1974).

Carriers which are suitable for the process of preparing siderophoric compositions using microbial siderophores are those which have active surfaces; the active surfaces have functional groups which can bond to a compatible functional group of the chosen siderophoric compound. The functional group can, for example, be selected from the class consisting of

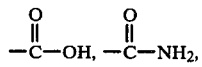

—(CH$_2$)$_n$—NH$_2$, n being 0, 1, 2, 3, etc.

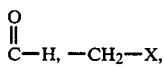

X being a halogen atom, for example, Br,

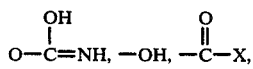

X being, as defined above,

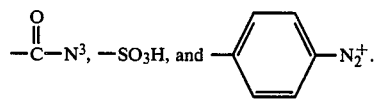

However, any functional group can be used which will react with a functional group on the microbial siderophore in question to bind it to the carrier, the microbial siderophore retaining its iron chelating capacity.

It is possible to put some distance between a microbial siderophore and the surface of the carrier, e.g. in order to limit the effect on the microbial siderophore of a surface characteristic of the carrier. For example, teflon may be used as a carrier. However, teflon has a highly hydrophobic surface which is non-wetting. Therefore, it is desirable to put some distance between the surface of the teflon and the microbial siderophore to allow the siderophore to extend well into an aqueous liquid medium.

A spacer compound may be used to provide a spacer group to space apart a carrier and a siderophore.

A suitable spacer compound is bifunctional; i.e. it has a functional group which can react with a functional group of the carrier to bind it thereto; and it has also a second functional group which can react with a compatible functional group on the chosen microbial siderophore to bind it thereto: see the above groups. The spacer group may alternatively have a second functional group which while not reactive with a compatible functional group on the siderophore, may be convertible into such a group.

A spacer compound can, for example, in addition to the above referred to functional groups, include a hydrocarbon chain, the length of which is chosen in accordance with the distance which it is desired to place between the carrier and the siderophore. The spacer compound used may be 1-ethyl-3-(3-dimethylaminopropyl) carbodiimide hydrochloride salt or glutaraldehyde. However any compound can be used which will space the microbial siderophore from the carrier, the necessary or desired distance provided of course that it is bifunctional.

The spacer compound may be bound, to a carrier by making use of conventional reactions involving the formation of ester groups, amide groups, amino groups, diazo groups, ether groups, sulphonamide groups, amidino groups; the reaction may be a carbon-carbon condensation.

Thus a carrier suitable for the process of the present invention may be represented generally by the formula

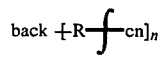

wherein n is an integer, "back" is a carrier backbone, "R" is a single bond or a suitable spacer group and "fcn" is a functional group as defined above. For example "fcn" may be a carboxyl group and R may be a group such as

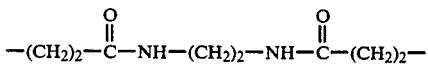

A useful carrier may need to have its surface treated in order to provide the surface with a suitable functional group which can bond to a microbial siderophore.

Thus silica (e.g. in the form of a silica gel) having surface hydroxyl groups can for example, be pretreated with a suitable ω-amino(C$_2$ to C$_{10}$ alkyl) tri (C$_1$ to C$_5$ alkoxy) silane to provide an active surface comprising amino groups. The silane can, for example, be γ-aminopropyltriethoxysilane. See, for example, the following patents wherein silica is treated with a silane: Canadian Pat. Nos. 1,102,347, 1,103,035 and 1,102,346; U.S. Pat. Nos. 4,203,952, 3,886,080, 3,904,373, 3,519,538, 3,652,761, 4,230,803, and 4,290,892.

Nylon, for example, is a carrier which requires a pretreatment to provide it with suitable functional groups. Since the nylon contains the amide group, its surface may be subjected to partial hydrolysis using known techniques to give free amino and carboxyl functional groups. The aqueous method may proceed as below:

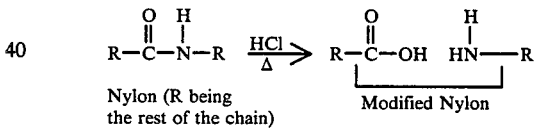

Nylon (R being the rest of the chain) → Modified Nylon

Alternatively, nylon can be reacted in a non-aqueous medium with, for example, thionylchloride to give rise to the functional group

If desired, an appropriate spacer group can be readily attached through, for example, the use of ethylene diamine or another functionally equivalent species such as

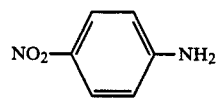

followed by a reduction of —NO$_2$ to —NH$_2$ suitable for generation of diazonium salts which are then suitable for coupling to a microbial siderophore, e.g. enterobactin. Succinic anhydride can thereafter be used as a further extension of the spacer group; i.e. to form an amide linkage.

Teflon is another useful carrier which must be pretreated in order to provide it with a suitable functional group which can bond to a microbial siderophore.

Teflon, a tradename for polytetrafluoroethylene from DuPont, is highly inert and is not readily attacked by acids and bases. No easy displacement of the fluorine atomes is known. Fluorine atom can, however, be displaced by ion-radicals such as sodium or potassium napthalene of formula:

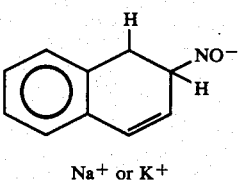

Na+ or K+

On reaction between teflon and such sodium or potassium naphthalene, a sodio or potassio species of teflon is formed of formula:

These organo metallic species of teflon are highly reactive towards many organic functional groups and their general behaviour is similar to the well known Grignard reagents. Thus, they can be reacted with a dimethyl carbonate to give rise to an alkoxy carbonyl substituted polytetrafluoroethylene. This substituted ethylene can subsequently be subjected to hydrolysis to provide a polytetrafluoroethylene with carboxyl substituents. The carboxylated teflon thus generated, can then be used for direct coupling to microbial siderophores (or chelators) such as "Desferal". As indicated above, it may be desired to space the siderophore from the surface of the teflon. If so, ethylenediamine and similar compounds can be readily attached through the carboxyl group by standard procedures. Since the teflon's backbone is very inert to many organic and inorganic reagents, very vigorous reaction conditions can be employed in further derivatization using the carboxylic functional group. See, for example, "Methods in Enzymology" Supra.

As indicated above, the microbial siderophore must also possess compatible functional groups which will react with those of the carriers without interfering with the chelating activity thereof. For example, suitable functional group in the siderophore enterobactin is the 2, 3-dihydroxy benzoic group which is susceptible to diazonium coupling under neutral to almost neutral conditions. The acylamine required in the generation of diazonium salts can be prepared from aminopropylsilylated glass.

Examples of suitable functional groups on the microbial siderophores are the amino group, the carboxyl group, the phenolate group and the cathecolate group, etc.

The previous comments relating to carriers, spacer groups etc for microbial siderophores apply to the use of other organic chelating (e.g. siderophoric) compounds, for example a catechol compound. If a catechol compound is used as the chelating compound, it may be bonded to a carrier by diazo coupling or through reaction with a functional group on the carrier such as

In these latter cases the functional group on the carrier is directly reactive with the benzene ring of the catechol.

The preparation of a composition comprising unsubstituted catechol suitably fixed to a silica gel carrier can be graphically described as follows:

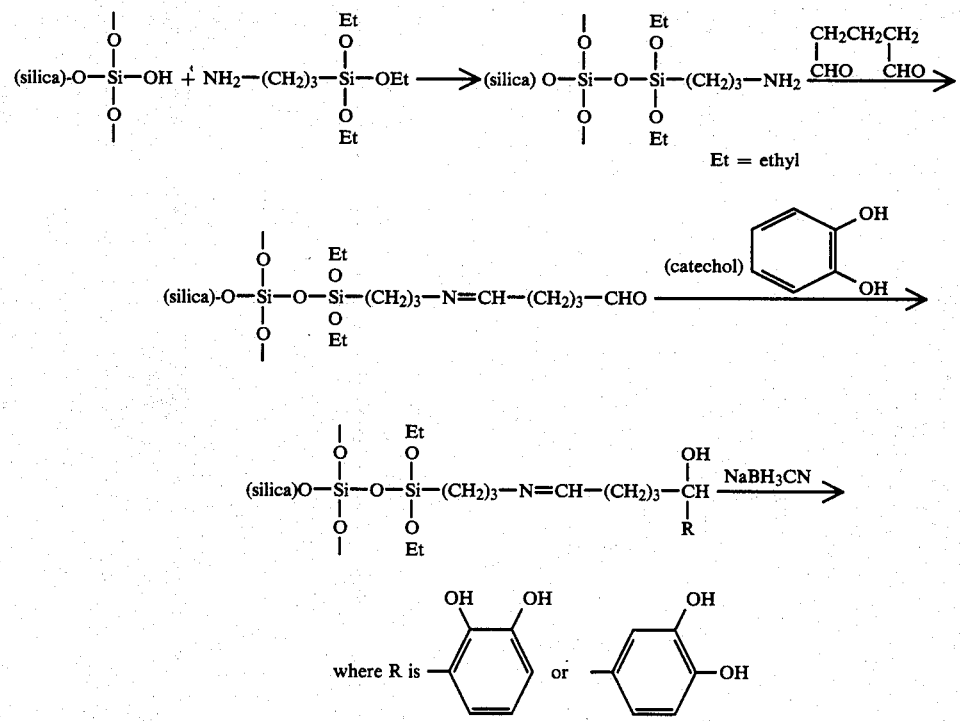

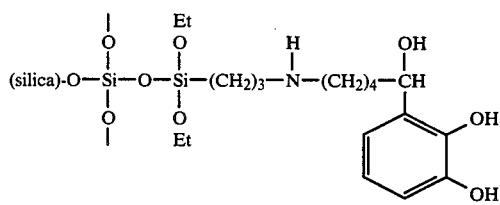 and 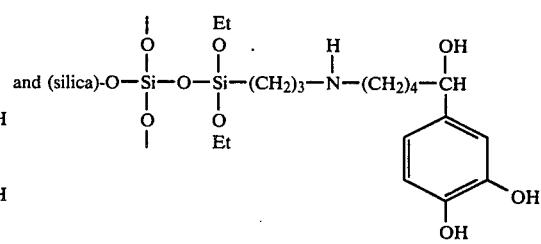

The above catechol compositions will hereinafter be referred to as

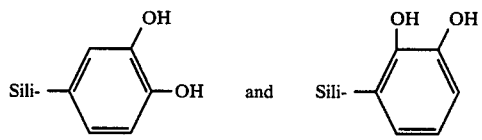

The above catechol compositions, e.g. Sili

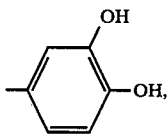

if stored for a prolonged period of time loaded with $Fe^{3+}$, undergo a chemical change whereby the composition gradually looses chelating activity. It is believed that this loss of activity is due to the reciprocal oxidation of the catechol and reduction of $Fe^{3+}$ (i.e. $Fe^{3+} \rightarrow Fe^{2+}$). The activity of the composition may be recovered by treating the composition with a suitable reducing agent such as will be discussed further on.

It has been determined that catechol compounds selected from the group consisting of catechol substituted on the benzene ring by one or more electrophilic substituents (i.e. the ring is mono or di-substituted) not only have an activity similar to that of unsubstituted catechol but have the additional advantage that they are better able to maintain their activity notwithstanding prolonged periods of iron loading. Accordingly these compounds can be used in circumstances where it is desired to avoid a reduction treatment. The substituents can be added to the benzene ring once catechol is fixed to the desired carrier. The substituent can be chosen for example from the class consisting of Halogen atoms (e.g. Cl and Br), NO, NO₂, COOH and

The ring can be mono or di halo substituted or mono substituted with NO or NO₂. The substituted catechol residues may thus have the following formulae

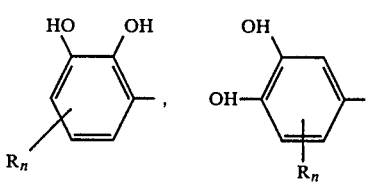

wherein R is a substituent as defined above, n may be 1 or 2.

When using a composition in accordance with the present invention, the conditions of use should of course be such as to avoid the break-down or decomposition of the composition; i.e. conditions such as <<pH, temperature, pressure, etc.>> should be chosen so as to avoid the break-down of the composition.

As indicated above, an insoluble (siderophoric) composition, in accordance with the present invention, can be used to remove iron from a liquid medium. In use, the (siderophoric) composition is intermixed with a desired liquid medium for a suitable time, which will of course depend upon the amount of (siderophoric) composition used, the initial iron concentration, the desired final iron concentration, etc. The $Fe^{3+}$ in the medium combines with the (siderophoric) composition and can thus be physically separated from the medium. The affinity of (siderophoric) compounds for iron can be so great that even small amounts of iron can be removed from a liquid medium. The final concentration of iron in a treated nutrient medium can for example be far below that required to support microbial growth.

In drawings which illustrate the present invention

Figure 2:
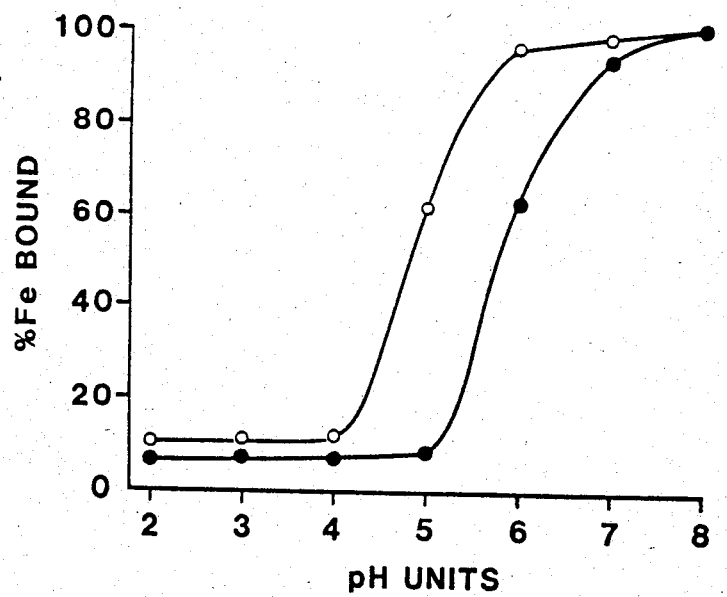
Figure 3:
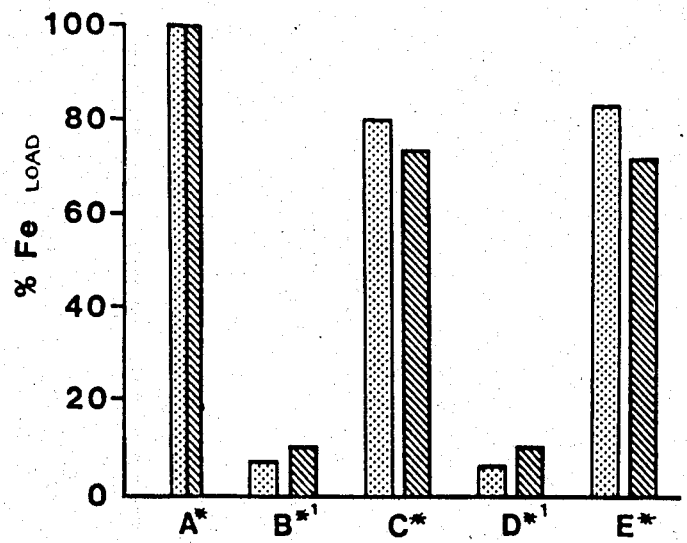

FIG. 1 is a graph illustrating the inhibition of microbial growth due to the removal of iron from a liquid medium, FIG. 2 illustrates regeneration of a siderophoric composition by pH manipulation; and FIG. 3 illustrates regeneration of a siderophoric composition by a reducing agent.

FIG. 1 as indicated above is a graph illustrative of the inhibition of microbial growth in even the most nutritional solutions (e.g. bacteriological broth media) on removal of iron therefrom.

In particular, FIG. 1 illustrates the inability of the bacterium *Neisseria meningitidis* to grow in a complex highly nutritional medium (neisseria defined medium—NDM) from which only iron has been extracted with ferrioxamine immobilized on agarose, the agarose having previously been activated by cyanogen bromide for coupling to ferrioxamine. Thus, one gram of the above siderophoric composition was contacted with 200 ml NDM at 22° C. for a time period of 20 min. before recovering the siderophoric composition. Prior to treatment, the NDM contained about 3.6 μM of iron;

after treatment, it contained less than 0.1 μM iron. The treated medium was then divided into two portions and FeCl$_3$ was added to one of them. A control consisting of untreated NDM and the two portions were then inoculated with microbes and maintained at a pH of 7.4 and a temperature of 37° C. As can be seen in FIG. 1, unhibited growth occurs in the control (0). However, in the treated medium, (●), cells are unable to undergo anymore than one or two divisions due to the absence of the vital nutrient iron. On the other hand if exogenous iron is added back to the treated medium full growth is again realized (▲).

Liquid media to be treated to remove Fe$^{3+}$ can have, for example, a pH in the range of 4.5 to 9. During the contact with the siderophoric composition, the temperature of the mixture can for example range from 1° C. to 50° C. and the contact can occur under atmospheric pressure. Examples of different media which can be treated with the composition are listed in Table 2 which follows:

TABLE 2

| Classes of liquid media | Specific example thereof |
|---|---|
| Liquid foods | fruit and vegetable juices, clear meat broth (e.g. consomme), culture media for microbial, plant and animal cells |
| Beverages | wine, beer, natural and synthetic juices, cider, drinking water |
| Pharmaceutical | buffer solutions for lavage (e.g. ophthalmic solution, peritoneal lavage), water used in the manufacture or various solutions and preparations, antibiotic solutions, |
| Cosmetics (liquid) | those susceptible to microbial degradation, contamination, or spoilage |
| Industrial water and waste water | cooling tower, process and waste water |
| Natural water | removal of actinides (e.g. Th$^{4+}$, UO$_2^{2+}$) and chromium |

A siderophoric composition can, as indicated above, for example, be used to remove iron from microbial fermentation cultures to stop further growth of microbes in the fermenter. Thus, a siderophoric composition in accordance with the present invention may be used to treat wine in order to inhibit microbial growth therein.

The composition of the present invention may also be used to remove iron from cosmetic solutions to prevent contamination by the growth of microbes. Components for cosmetic solutions are often obtained from natural sources and are susceptible to microbial degradation.

A siderophoric composition of the present invention may also be used for the removal of iron from drinking water, pharmaceutical and biological solutions, and industrial water.

Although the microbial siderophores are selective for iron, they can also bind metals that are classified as actinides e.g. uranium. Thus, the present invention additionally provides means for removing such hazardous metals as plutonium from contaminated water; and a rapid means to collect (concentrate) the radioactive heavy metals (e.g. plutonium) to determine the concentration thereof in standard water volumes. Such metals are selectively removed from water due to their structural similarity (i.e. atomic) to iron.

As indicated previously, compositions in accordance with the present invention, may possibly be regenerated for further use by the removal of the metal therefrom by suitable chemical means. In this way, the composition can be economically used since it can be recycled for repeated use.

The regeneration, for example, of a (siderophoric) composition loaded with iron, may be carried out either through the manipulation of the pH of a medium surrounding the iron-loaded (siderophoric) composition and/or by treating the iron-loaded composition with a suitable reducing agent. In either case, appropriate conditions should be chosen which will not decompose the composition or destroy the iron binding capacity thereof.

If regeneration is affected by manipulation of the pH, the pH must be brought to or beyond a point at which the iron is released.

In general, when making use of a microbial siderophore, a pH of 1 or lower should be avoided; the use of mineral acids should also be avoided. The pH can be manipulated through the use of organic acids (for example, acetic acid, succinic acid, citric acid, isocitric acid, ketomalonic acid, malic acid, oxalic acid or pyruvic acid).

If a catechol compound is used a mineral acid may be used to manipulate the pH.

FIG. 2 illustrates the regeneration of a (siderophoric) composition by the manipulation of pH. The designation (●) represents enterobactin immobilized on a polyacrylamide carrier whereas the designation (O) represents desferrioxamine immobilized to the same type of carrier. The pH was lowered in the presence of 15 mM citrate and 0.05M tris-sodium acetate. The lowering of the pH was accomplished by an addition of appropriate amounts of acetic acid.

Alternatively, an iron loaded composition may be treated with a suitable reducing agent to release the iron. In accordance with the present invention, it is possible to use suitable dithionites or ascorbates as the reducing agents, e.g. sodium or potassium dithionite and sodium or potassium ascorbate. The dithionites can be used for the reduction of (siderophoric) compositions which include hydroxamate ligands whereas the ascorbates can be used for the reduction of siderophoric compositions containing phenolate/catecholate group ligands. Other useful reducing agents include hydroxylamine and hydroquinone.

The compositions wherein the organic chelating compound includes catecholate ligands (e.g. siderophoric compositions consisting of enterobactin fixed to glass) and especially the compositions containing diazo linkages must be subjected to mild reduction conditions such as provided using ascorbic acid. The compositions which include hydroxamate groups (Desferal), can be reduced with 1.0 molar sodium dithionite.

Other reducing agents may possibly be used to regenerate a composition; however, the reducing agent used must be chosen on the basis that it will not destroy the integrity or metal-binding (e.g. iron-binding) capacity of the composition. Sodium dithionite (Na$_2$S$_2$O$_4$), hydroxylamine (including its acid addition salts) and hydroquinone are as indicated above examples of useful reducing agents. In particular the reducing agent can be hydroxyl amine chloride.

The regeneration of a (siderophoric) composition may take place in the presence of a suitable organic acid that will complex with the iron that is released. Suitable acids are di or tricarboxylic organic acids that will chelate the liberated iron ions.

FIG. 3 illustrates the repeated regeneration of (siderophoric) compositions consisting of enterobactin (▨) desferrioxamine (▦) bound to polyacrylamide carriers, the reducing agent consisting of sodium ascorbate. The regeneration solution had a pH of 7 in the presence of 15 mM sodium citrate and 0.05M sodium acetate.

Compositions in accordance with the present invention which are loaded with $Th^{4+}$ and/or $UO_2^{2+}$ may possibly be regenerated in the same manner as for iron loaded compositions. When regenerating a composition loaded with $UO_2^{2+}$ by manipulation of pH a relatively low pH (e.g. pH≅0.8) may be needed to remove this ion; accordingly it may be necessary to resort to the use of a mineral acid to recover the ion e.g. HCl. Less severe condition may be used to recover the $Th^{4+}$ e.g. by using a wash solution having a higher pH than that necessary for the removal of $UO_2^{2+}$.

Since the $Th^{4+}$ may be recovered at a higher pH than the $UO_2^{2+}$ it is possible to manipulate the pH of the solution to be treated such that a composition in accordance with the present invention will preferentially take up the $UO_2^{2+}$ thereby separating $UO_2^{2+}$ from $Th^{4+}$.

Alternatively as indicated above, an insoluble composition in accordance with the present invention may be used to take up both $UO_2^{2+}$ and $Th^{4+}$. The so obtained composition may then be treated with an aqueous solution containing a suitable $Th^{4+}$ chelating agent and an organic acid, the pH of the solution being greater than 2.

Preferably the pH of the aqueous solution should be about 4 to about 6.

Some of the above referred to microbial siderophores in free form (i.e. not fixed to a carrier) may possibly be used to chelate $Th^{4+}$ for the above method. Alternatively the ion chelating agents disclosed in Archibald, F. A. and I. W. DeVoe 1980, Iron acquisition by Neisseria meningitidies in vitro Infect. Immun 27:322-334, are suitable for chelating $Th^{4+}$.

The chelating agent and the organic acid may both be a tricarboxylic acid; they may be the same. It is possible to provide the necessary tricarboxylic acid by adding a mineral acid (e.g. HCl) to an aqueous solution containing an alkali metal salt of a suitable tricarboxylic acid e.g. $Na_3$ citrate.

Suitable $Th^{4+}$ chelating agents may be selected from among organic acids having the following general structures

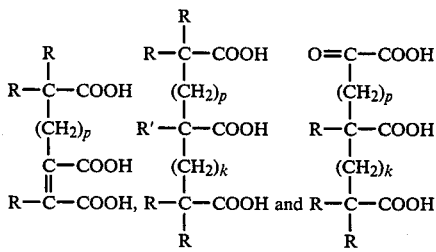

wherein R' and each R are independently selected from the group consisting of hydrogen and suitable organic residues; R' may also alternatively be OH or alkoxy ($C_1$ to $C_{10}$); p and k are the same or different and are 0 or an integer; R', R, p and k are selected such that the chelating activity of the three COOH groups is not interfered with. R can for example be selected from alkyl (e.g. $C_1$ to $C_{10}$); Halogen (e.g. Cl, Br); p and k may possibly be 1 to 10.

Preferably each R is H and p and k are 0.

Suitable chelating agents are citric acid, isocitric acid, cis-aconitic acid and oxalosuccinic acid. The alkali metal salts of these acids could of course be used in conjunction with a suitable source of protons (i.e. $H^+$) e.g. a mineral acid such as HCl.

The organic acids may be selected from the same group of acids as outlined above for the $Th^{4+}$ chelating agents. However, other organic acids may be used such as the mono and di carboxylic acids (e.g. acetic acid, malonic acid etc.).

A pH for the aqueous solution of greater than 2 is necessary in order to inhibit the simultaneous removal of $UO_2^{2+}$ from the composition i.e. at a pH lower than 2 $UO_2^{2+}$ can be recovered from the composition. Thus once $Th^{4+}$ is separated from the composition it is possible to recover a concentrated solution containing $UO_2^{2+}$ by subsequently treating the composition with an aqueous solution having a low pH. As indicated above since it may be necessary to use a mineral acid in order to recover $UO_2^{2+}$ the composition in such case can be based on a catechol compound; the catechol compound is preferably fixed to a silica gel if the $UO_2^{2+}$ is to be recovered and the composition reused.

The insoluble compositions in accordance with the present invention thus provides for the advantageous removal of metals (e.g. iron) from liquid media. Such media remain essentially unchanged except for the absence of metal. The liquid media referred to herein may be aqueous, organic or mixtures thereof.

Reference will now be made to a number of examples which deal with embodiments of the present invention.

EXAMPLE 1

Activation Of Silica Gel (glass)

The activation methods were analogous to those as described by H. Weetal & A. M. Filbert, Methods of Enzymology XXXIV B:59-72 1974.

(a) Pretreatment 100 grams of silica gel designated Sigma S-4133 (sold by Sigma Chemical Company) of 100 to 200 mesh (70 to 140 microns) chromatographic grade and of pore diameter of about 25 angstrom was suspended in a mixture of 50 ml of 70% $HNO_3$ and 300 ml of distilled water. The suspension was refluxed with mixing for about 1 hour.

The gel was allowed to settle and the liquid layer drawn off. The gel was then washed repeatedly with distilled water until the wash water was about neutral pH.

(b) Amine activated silica gel

The above pretreated silica gel (wet) was used for the following amination without drying. A 10% solution of γ-aminopropyltriethoxysilane in distilled water (500 ml) was added to the above obtained silica gel. The pH was then adjusted to 3.45 with 6N hydrochloric acid. The suspension was then maintained under stirring at a temperature of 75° C. for about 3 hours. The gel was then filtered and washed with 500 ml of distilled water and dried in an oven at 100° to 110° C.

The above amination can be described graphically as follows:

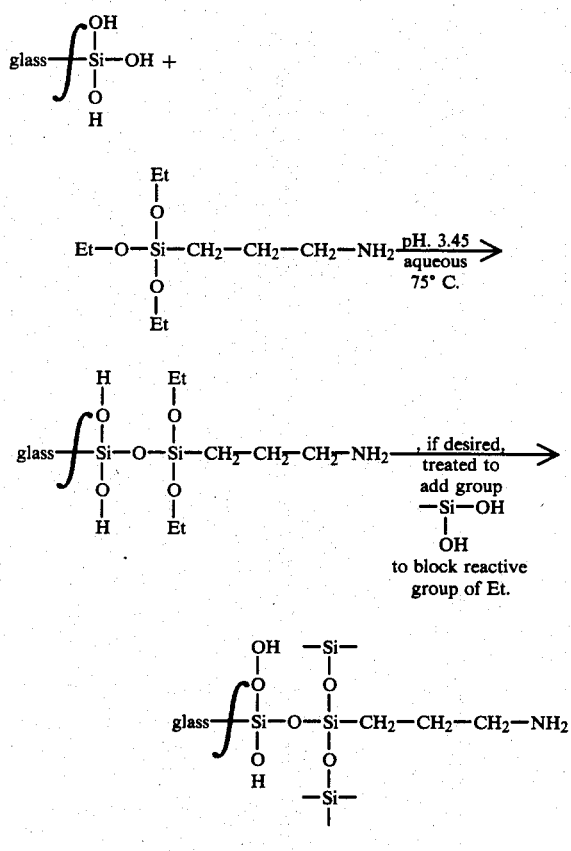

Et = ethyl

The above obtained amineactivated silica gel will hereinafter be referred to as glass ⨍-NH₂

(c) Aminoarylcarbonyl activated silica gel 50 grams of glass ⨍-NH₂ was suspended in 300 ml of ethanol free chloroform. 2.5 grams p-nitrobenzoyl chloride [Eastman Kodak] was subsequently admixed therewith. Thereafter, 30 ml of dry triethylamine was added and the resultant mixture was refluxed for 20 hours. The beads were allowed to settle and the liquid phase drawn off. The beads were then wash repeatedly with chloroform then repeatedly with ethanol and finally with distilled water with ethanol. The wet water-washed gel was subjected to a treatment for the reduction of the nitroaryl group to an aminoaryl group by adding the gel to a solution of 50 gm of sodium dithionite in 250 ml. of distilled water. The whole suspension thereafter being refluxed with mixing for 45 min. The suspension was then filtered while still hot and washed repeatedly with dilute hydrochloric acid and then washed with distilled water. After thorough washing with distilled water, the gel was dried in an oven at 70° to 80° C.; this type of activated carrier can be used for subsequent diazotization and coupling.

The above reaction can be represented graphically as follows:

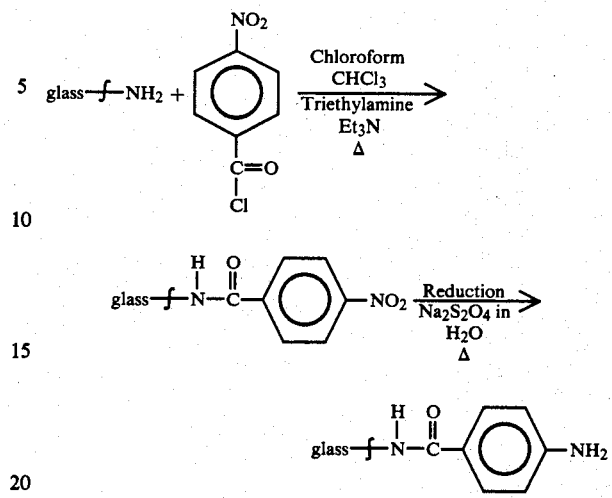

(d) Carboxyl activated silica gel 50 gm of glass ⨍-NH₂ (see above), were suspended in 250 ml of water cold in an ice bath. 50 ml of 1N sodium hydroxide was added followed by 15 gm of solid succinic anhydride. After mixing for 2 hours, the pH was adjusted with the addition of 1N sodium hydroxide to a pH of 5-6. This adjudtment of pH with sodium hydroxide was repeated hourly three additional times and the mixture was left overnight. The suspension was thereafter filtered and washed thoroughly with distilled water and dried at 100° to 120° C.

The above reaction can be represented graphically as follows:

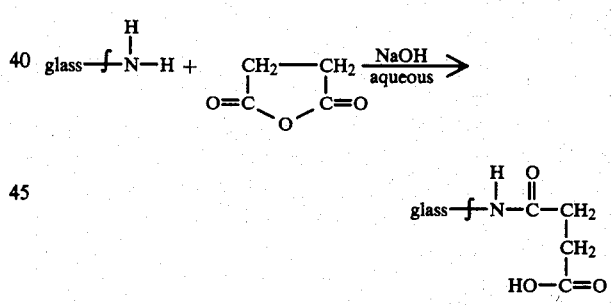

(e) Aldehyde activated silica gel 20 gm of glass ⨍-NH₂ (see above) were suspended in 50 ml of 0.1M sodium phosphate at a pH of 7 followed by the addition of 10 ml purified 8% glutaraldehyde. The mixture was subjected to vacuum and mixed occasionally. The reaction was allowed to proceed for 3 hours and the mixture was thereafter filtered, washed thoroughly with distilled water and dried under vacuum.

The reaction outlined above can be represented graphically as follows:

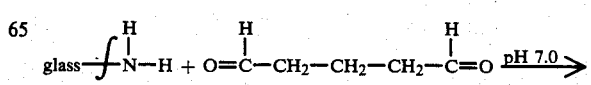

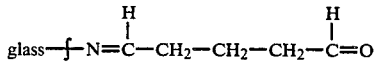

EXAMPLE 2

Activation Of Polyacrylamide (Azide Coupling)

60 ml of ethylene diamine activated polyacrylamide gel (per Inman, Methods in Enzymology XXXIV B:35 1974) was diluted with water to make up to 100 ml volume. About 1.2 g of p-nitrobenzoyl azide was dissolved in 100 ml of tetrahydrofuran and the obtained solution was subjected to filtration. The obtained filtrate was added immediately to the aqueous gel suspension referred to above. 1.5 ml of triethylamine was then added to the suspension. The gel mixture was then stirred gently for 30 min. An additional portion of 1.2 grams of p-nitrobenzoyl azide in 50 ml of tetrahydrofuran was added followed by another 1 ml of triethylamine. Gentle stirring was continued for an additional hour. The obtained gel was filtered and washed thoroughly with 1:1 tetrahydrofuran:0.2M sodium chloride and then resuspended in 0.2M sodium chloride. 3 ml of acetic anhydride was added to the suspension which was then mixed for 1 hour, the gel being thereafter washed with 0.1M NaCl.

The obtained gel can be used directly for diazo coupling. The reaction can be represented graphically as follows:

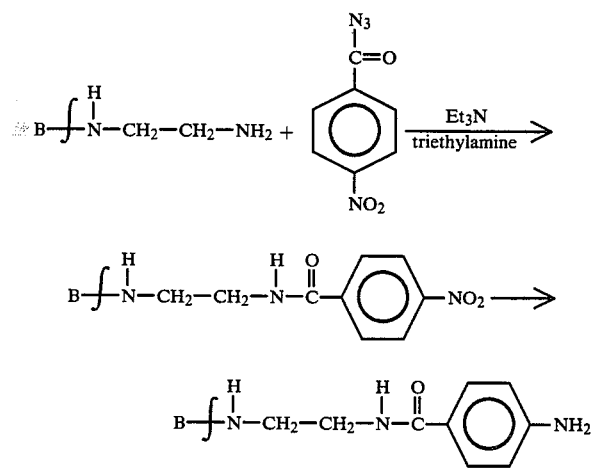

wherein: B = polyacrylamide backbone (ie carrier)

EXAMPLE 3

Activation Of Agarose With Cyanogen Bromide

Agarose swollen in water was mixed with an equal volume of water. Finally divided CNBR (50–300 mg per ml of agarose) was added at once to the stirred suspension. The pH of the suspension was immediately adjusted and maintained at pH 11 with sodium hydroxide. The temperature of the suspension was maintained at 20° C. and the reaction allowed to proceed for about 30 min. Thereafter, the gel was then washed rapidly with a large amount of ice cold water followed by washing with an appropriate buffer. The obtained activated gel should be used as soon as possible.

The chemical reactions involved in the agarose activation can be indicated graphically as follows:

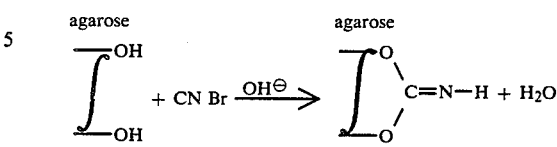

Cyanogen bromide, by analogous procedures, can be used to activate other polysaccharides; for example, alginate, glucans, cellulose, agar, dextrans, etc.

EXAMPLE 4

Immobilization Of Ferrioxamine Or Enterobactin 1 mM HCl-washed, water swollen CNBR activated carrier, obtained in accordance with Example 3, was mixed with ferrioxamine or enterobactin (20 mg/ml) in an NaHCO$_3$ buffer (0.1M, pH 8.3) containing 0.5M NaCl. The mixture was agitated overnight at 4° C. The gel was then washed with 0.1M acetate buffer pH 4.0 containing 0.5M NaCl to remove excess uncoupled ferrioxamine or enterobactin.

EXAMPLE 5

Immobilization Of Desferal To Polyacrylamide Gel (a) Biogel P-150 polyacrylamide from BioRad was linked through ethylenediamine and then succinic anhydride following published procedures as described by Inman (John K. Inman, Covalent Linkage of Functional Groups, Ligands, and Proteins to polyacrylamide beads in "Methods of Enzymology", XXXIV B, 30 (Jakob, W. B. ed.) Academic Press, New York (1974) and Biochemistry 8:4074 (1969); (see examples 16 and 17) infra. Unreacted free amino groups in ethylene-diamine were blocked by reaction of acetic anhydride at the end of the reaction period. Test for presence of any free amino group was through the TNBS (trinitrobenzene sulfonic acid) test. The addition of acetic anhydride was repeated twice until TNBS test were negative.

This activated, extended polyacrylamide was immediately used for coupling.

(b) Coupling of Desferal to activated polyacrylamide gel 700 mg Desferal was dissolved in 5 ml of deionized water and followed by addition of 163 mg ferric chloride. A deep red solution was formed. 20 ml activated gel, obtained above, was washed twice with ethanol by centrifigation and decantation. The total solid shrank to a very small volume after the second volume of ethanol (20 ml) was added. The 5 ml of ferric complexed Desferal was added at 20° C. to this shrunken gel and the mixture was mixed by swirling. The gel gradually swelled to give a solid mass. 5 ml of H$_2$O was added to help disperse the gel and the pH of the suspension was adjusted to 4.2 with NaOH (1N). 200 mg EDC (1-ethyl-3-(3-dimethylamino propyl)carbodiimide), 200 mg was added in one portion and the pH of the suspension monitored and kept at 4.3 to 4.6 by addition of HCl (1N), for 3 hrs. A further portion of 200 mg EDC was added and the mixture, allowed to stand overnight at room temperature. The gel was filtered on a sintered glass funnel and washed with 0.2M NaCl.

The reaction can be graphically represented as follows:

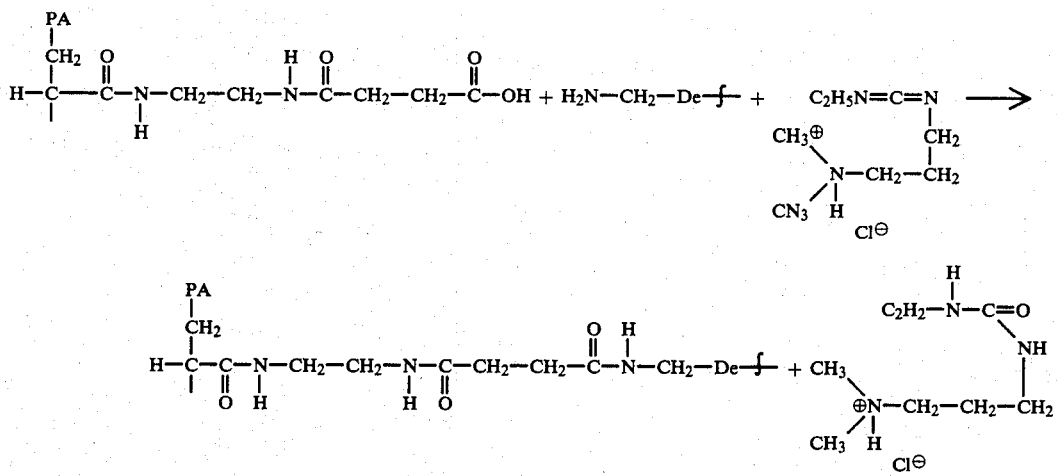

wherein:
PA=polyacrylamide backbone or carrier and
De—│—=desferal.

EXAMPLE 6

Immobilization Of Ferrioxamine Or Enterobactin To Polyacrylamide Carrier

A swollen polyacrylamide gel acyl azide derivative freshly prepared as in accordance with example 2 was suspended in a solution containing the following: 0.1M $CaCl_2$, 0.001N HCl acid, ferrioxamine or enterobactin at 0.3 mg/ml (pH 4.0). The pH was immediately adjusted to 9.0 and the mixture was stirred for 60 min. at 0° C. In the case of enterobactin, the solutions are 50% ethanol. The coupled gel was washed with large volumes of 0.05M Tris-acetate-0.15M citrate, pH 7.0.

EXAMPLE 7

Immobilization Of Desferal To Silica Gel (Glass Beads)

About 700 mg (or approximately one mMole) of Desferal was dissolved in 25 ml of water followed by the addition of 170 mg of ferric chloride. The pH of the solution was then adjusted to 4.3 with one normal hydrochloric acid and to this was added 25 gm of succinylated silica gel characterized by the formula:

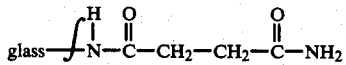

200 mg of EDC:HCl was added to this mixture which was thereafter agitated for 3 hours at room temperature. The pH of the solution was then adjusted to 4.3 and the mixture allowed to stand overnight. After filtration, the obtained composite was washed thoroughly with distilled water until the washing water was colorless. Thereafter, the obtained composite was dried under vacuum.

EXAMPLE 8

Immobilization Of Enterobactin To Aminoarylcarbonyl Activated Silica Gel 5 gm of aminoarylcarbonyl activated silica gel obtained as in step (c) of example 1, was mixed with 10 ml of 1M sodium nitrite and cooled in an ice bath. 1 ml of concentrated hydrochloric acid was added dropwise to the cooled solution. The mixture was maintained in the ice bath for an additional 45 min. to allow for complete diazotization. The mixture was then filtered in the cold, washed with cold distilled water and, while still cold, the gel was added to a solution of about 30 mg of enterobactin in 10 ml of ethanol including about 2 ml of saturated borax solution. The reaction was allowed to proceed for 1 hr in an ice bath. The composite was then recovered by filtration and washed with an ethanol water mixture containing 0.1 normal hydrochloric acid and thereafter with ethanol until the filtrate obtained was colorless. The obtained composite was then dried under vacuum.

The coupling reaction can be represented graphically as below:

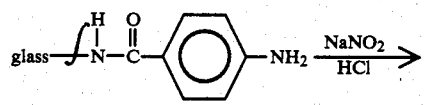

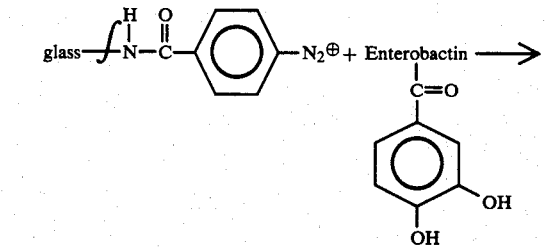

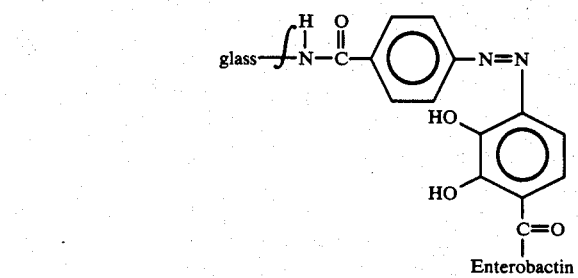

EXAMPLE 9

Immobilization Of Cathechol To Polyacrylamide Gel: Diazo Coupling 20 ml of the gel obtained in accordance with Example 2, was suspended in 20 ml of 0.1 normal HCl and cooled in an ice bath. While the suspension was maintained in contact with the ice bath, 2 ml of 1M sodium nitrite was added dropwise with agitation of the suspension. The resultant mixture was kept in the ice bath for an additional 30 min. and centrifuged to remove the liquid phase. The gel was then washed twice with ice-cold distilled water and then placed in contact with 20 ml of an ice-cold solution of 10% catechol in saturated borax. The reaction was allowed to proceed overnight at 4° C. The composite was recovered by filtration and it was washed repeatedly with water containing 0.1 normal HCl. The reaction can be indicated schematically as follows:

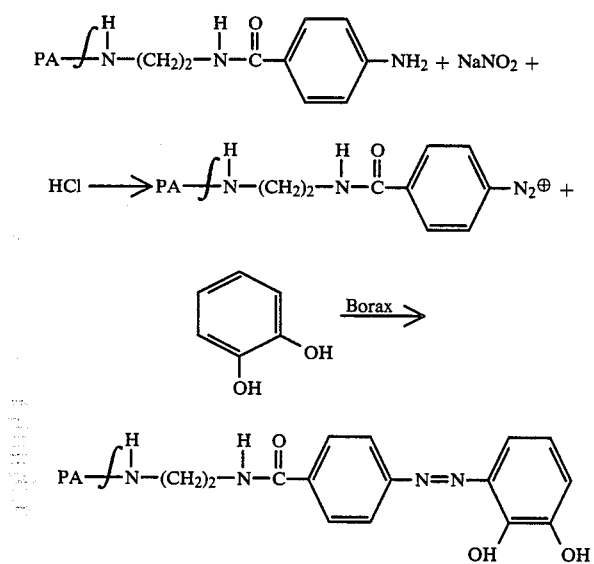

wherein PA is polyacrylamide carrier or backbone.

EXAMPLE 10

Immobilization Of Catechol To Aminoaryl Carbonyl Activated Silica Gel 20 gm of aminoarylcarbonyl activated silica gel obtained in accordance with example 1 (c) was suspended in 20 ml of ice-cold water. 10 ml of 1M sodium nitrite was added to the suspension while maintaining the suspension in an ice bath. 10 ml of 2 normal hydrochloric acid (ice-cold) was slowly added dropwise to the suspension. The reaction was allowed to proceed at between 0° and 4° C. for about 1 hour and it was then washed with ice-cold distilled water. The solid was then added to 10 ml of 10% cathecol in saturated borax solution (ice-cold) with mixing. 20 ml of water was added to facilitate mixing and the reaction was allowed to proceed in an ice bath for an additional one hour. The composition was then allowed to settle and the liquid siphoned off. The composition was washed with distilled water containing 0.1 normal hydrochloric acid and ethanol. The composition was repeatedly washed until the washing water was colorless. The composition was then recovered and dried under a vacuum.

The reactions involved with the catechol can be represented generally as below:

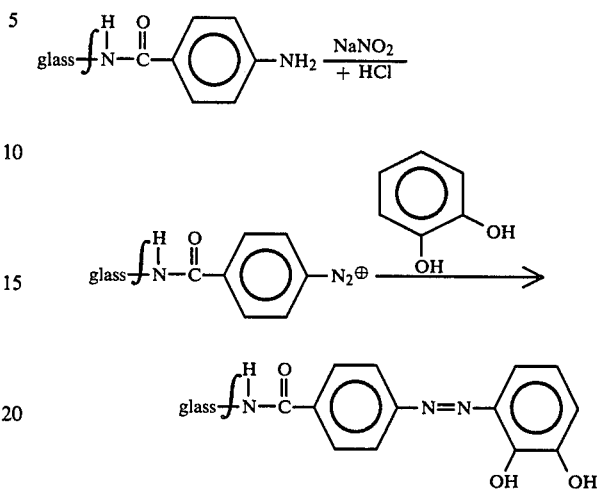

EXAMPLE 11

Immobilization Of Catechol To Aldehyde Activated Silica Gel 5 gm of aldehyde activated silica gel (activated as in examle 1 (e) above) was suspended in 10 ml of 10% cathecol in saturated borax solution for 1 hour. The mixture was then subjected to vacuum evaporation and then heated while still under vacuum at 70° C. for one hour. The mixture was then cooled to room temperature and water was added thereto, the mixture then being heated at 70° C. for an additional hour. The mixture was then cooled to room temperature and 500 mg of sodium borohydride was added and the mixture was maintained at 70° C. for a further hour. The resultant reaction mixture was then cooled in an ice bath and 5 ml of glacial acetic acid was added dropwise with mixing. The reaction was allowed to proceed for an additional 30 min. and the mixture was then filtered. The recovered composition was then washed repeatedly with distilled water and ethanol alternately and then dried under vacuum.

The general chemical reactions are believed to be as follows:

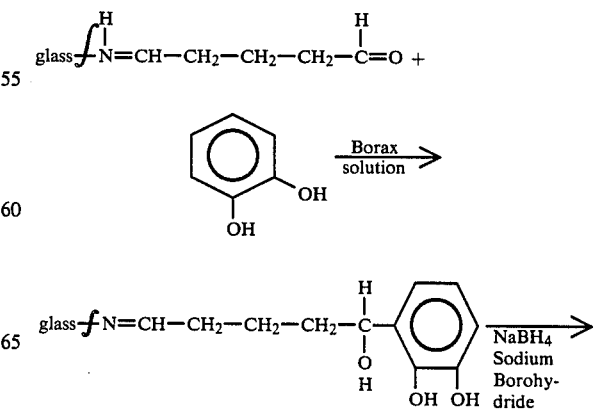

-continued

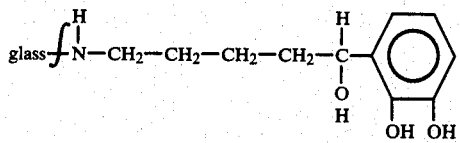

EXAMPLE 12
Removal Of Iron From Wine

The inability of wine to spoil after extraction of iron using the composition of the present invention is illustrated in table 3 below. This protection from spoilage is retained even when the wine is vigorously aerated (agitated continually in open flasks at 25° C.). The treatment of the commercial wine samples consisted of vigorously aerating the sample after inoculating with acetobacter xylinum, aeration continuing for a period of about 30 days at 25° C.

TABLE 3

| TREATMENT | OBSERVATIONS |
|---|---|
| None | By three weeks, wine was foul smelling (including acetic acid smell); turbid from bacterial growth |
| Filter sterilized (no bacteria added (0.45 μm pore size) | No spoilage |
| Iron extraction with siderophoric composition of the present invention | No spoilage |
| Addition of iron ions to wine subjected to iron removal by treatment with the siderophoric composition of the present invention | By three weeks, wine was foul smelling (including acetic acid smell); turbid from bacterial growth |

The following examples (i.e. 13 and 14) illustrate the procedure which may be used to recycle siderophoric compositions in accordance with the present invention i.e. recycling after removal of bound iron. The reuse of the siderophoric composition of the present invention makes it economically attractive.

EXAMPLE 13
Regeneration Of An Active Iron-Free Siderophoric Composition Comprising Enterobactin Fixed To Silica Gel The siderophoric composition subjected to regeneration can in general be represented by the following graphic formula:

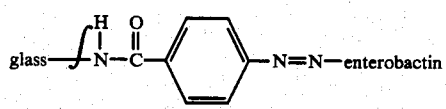

The above siderophoric composition loaded with iron, was subjected to treatment with an equal volume of 0.1M sodium citrate and 0.1M ascorbic acid, the treatment lasting for a period of about 12 hours. The treatment was repeated twice for a recovery of loaded iron in the range of 95%.

Repeated loading and unloading of the siderophoric composition with $Fe^{3+}$ results in retention of up to 95% of the original iron-building capacity.

On average, each gram of iron-loaded siderophoric composition included about 212 to 232 micrograms of iron per gram of composition. In the above procedure, about 80–100 mg. of siderophoric composition were subjected to regeneration.

EXAMPLE 14
Regeneration Of A Siderophoric Composition Comprising A Catechol Fixed To A Silica Gel (a) The siderophoric composition can be represented generally by the following graphic formula:

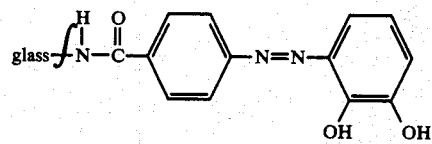

The siderophoric composition was subjected to the same treatment as in Example 13. The iron-loaded siderophoric composition contained from 110 micrograms to 163 micrograms of $Fe^{3+}$ per gram of the composition. Retention of iron-binding capacity after regeneration was up to 95%.

(b) The siderophoric composition having the following general structure was subjected to a reductive regeneration:

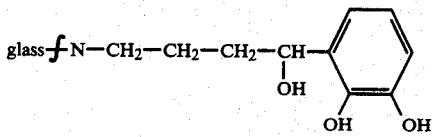

The iron loaded siderophoric composition contained from 43 micrograms to 56 micrograms or iron per gram of siderophoric composition. The siderophoric composition was regenerated using 5 ml of 0.1M sodium dithionite. Treatment in this way resulted in the recovery of 85 to 93% of the iron-binding capacity of the siderophoric composition.

EXAMPLE 15
A Siderophoric Composition Comprising Ferrioxamine Fixed to Silica Gel The siderophoric composition was obtained in accordance with the procedure outlined in Example 7. The siderophoric composition had an iron binding capacity of about 740 micrograms of iron per gram of siderophoric composition. 12 gm of the above composition when exposed to 5 ml of a 500μM $Fe^{3+}$ solution was able to remove or recover 79.1% of the iron; on being exposed to about 5 ml of a 5μM $Fe^{3+}$ solution about 98.8% of this iron was removed or recovered from the solution by the siderophoric composition.

EXAMPLE 16

Activation of Biogel P 150 with Ethylenediamine:

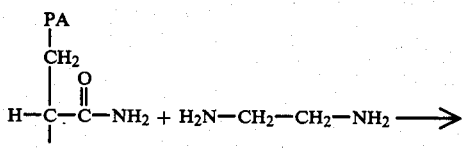

-continued

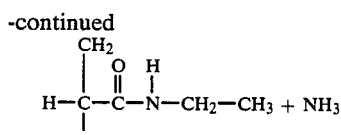

PA=polyacrylamide back bone:

All operations were carried out in a well ventilated hood. 200 ml. anhydrous ethylene diamine in a 500 ml. 3 necked round bottom flask was heated with a heating mantle and the final temperature was reached and adjusted and maintained at 90° C.±2° C. The glass was also equipped with a condenser with outlet protected by a drying tube, a mechanical stirrer and the third neck was used for addition of materials and temperature monitoring. 10 gm of Biogel-P 150 was added through the thermometer neck in one portion and the mixture was stirred and heated at 90° C.±2° C. for a period of 3 to 4 hours. The solid gel swelled to a great volume and the evolution of ammonia can be ascertained by wetted pH paper at the drying-tube outlet. At the end of the reaction, the mixture was poured with mechanical stirring on to a mixture of 400 ml, ice and water (1:1). Any gel adhering to the flask can be washed down by jets of water. The gel was filtered while the mixture was still cold. The gel was promptly washed repeatedly with 0.2M NaCl and 0.001N HCl until the filtrate gave a negative TNBS test (Trinitrobenzenesulfonic Acid). The total gel volume was about 170 ml. i.e. wet gel.

EXAMPLE 17

Succinylation: Carboxylic Arm Extension:

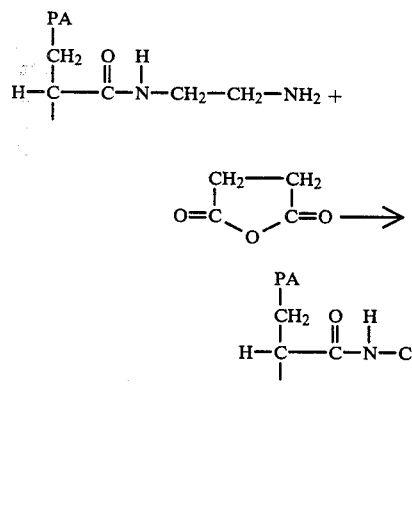

PA=polyacrylamide back-bone.

50 ml. wet gel (Biogel P-150-Ethylenediamine activated) is suspended in 50 ml. 0.1N NaOH in a 250 ml. beaker. External cooling in an ice bath and gentle mechanical stirring is also provided. 1.0 gm. succinic anhydride (10 mmole) was added in one portion and the mixture stirred in the cold for 2 hrs. A further 1 gm. portion of succinic anhydride was added with further cooling and stirring for an additional hr. During the addition of the second portion of succinic anhydride, the mixture pH is monitored intermittently with a pH meter and additional amounts of 1N NaOH were added to maintain a pH of 3.5 to 4.0. A third portion of 1 g. succinic anhydride was added and the monitoring procedure was same as the previous addition. The TNBS Test showed that there were still free amino group on the gel and these were blocked by addition 10 ml. acetic anhydride and stirred for 30 min. The mixture was eventually washed thoroughly with 0.1M NaCl. TNBS Test was negative for the gel.

For the following examples 18 to 21, the formula for the starting catechol composition is indicated as a matter of convenience as comprising a single isomer; the composition used was however a mixture of

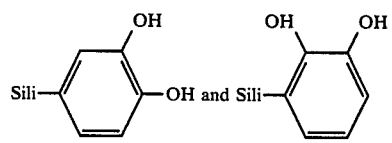

EXAMPLE 18

Preparation of a Chloro Substituted Catechol Composition

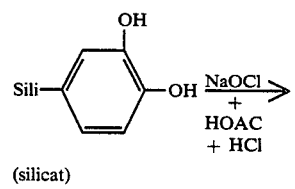
(silicat)

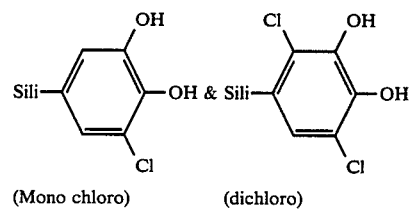
(Mono chloro)      (dichloro)

To one batch (prepared from 500 gm silica) of silicat was added 100 ml Commercial sodium hypochlorite (4–6% solution) and the mixture was stirred and cooled in an ice bath. 50 ml of glacial acetic acid was added and the mixture was stirred and evacuated simultaneously. Cooling in the ice bath continued for another 30 minutes. Then 50 ml concentrated hydrochloric acid was added and the mixture allowed to come to room temperature gradually. Stirring and evacuation continued for a further two hours and the mixture was then diluted with a large volume of water and filtered on a Buchner funnel. The solid was washed thoroughly with water first. Then it was soaked in 5% aqueous ammonia and washed with water again thoroughly. Then it was soaked in 5% hydrochloric acid and washed with water again. The solid is stored as a suspension in the acidified form for subsequent utilization.

EXAMPLE 19

Preparation of a Bromine Substituted Catechol Composition

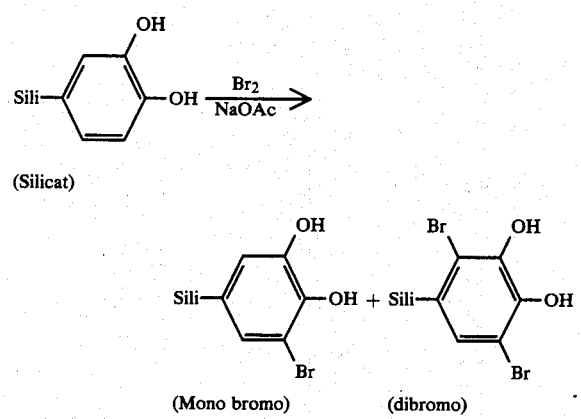

(Silicat)

(Mono bromo)   (dibromo)

To one batch (prepared from 500 gm. silica) of silicat was added 10 gm. sodium acetate and the mixture was cooled in an ice bath. This was followed by the addition of 5 ml. of liquid bromine and the mixture was stirred, evacuated and cooled in an ice bath simultaneously. The reaction was allowed to proceed in this manner for two hours and the obtained mixture was then washed thoroughly with water to eliminate all unreacted bromine. The mixture was then soaked in 5% ammonium hydroxide, washed with water and then soaked in 5% hydrochloric acid. It was finally washed thoroughly with water and stored in water in an acidified aqueous environment.

EXAMPLE 20

Preparation of NO Substituted Catechol Composition

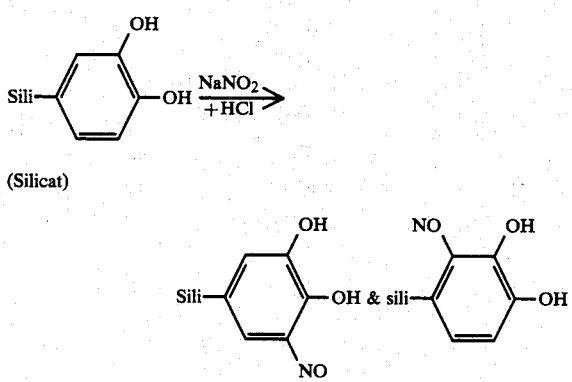

(Silicat)

One batch (prepared from 500 gm. silica) of silicat was cooled sufficiently in an ice bath and followed by the addition of 7.0 gm. sodium nitrite ($NaNO_2$). The suspension was stirred, evacuated and cooled in an ice bath simultaneously. The reaction was allowed to proceed for 30 minutes. This was followed by the addition of 10 ml. concentrated hydrochloric acid and a perceptible evolution of nitrogen oxide was observed. The reaction was processed as before for another two hours. The mixture was then washed thoroughly with water, soaked in 5% ammonium hydroxide which brings about a deepening of the color of the solid to a redder shade. The filtrate and aqueous washings were reddish orange and washing with water continued until the washings were colorless. The solid was then soaked in 5% hydrochloric acid which changes the color from reddish to a more orange shade and the suspension was washed thoroughly with water and stored in this acidified form.

EXAMPLE 21

Preparation of $NO_2$ Substituted Catechol Composition

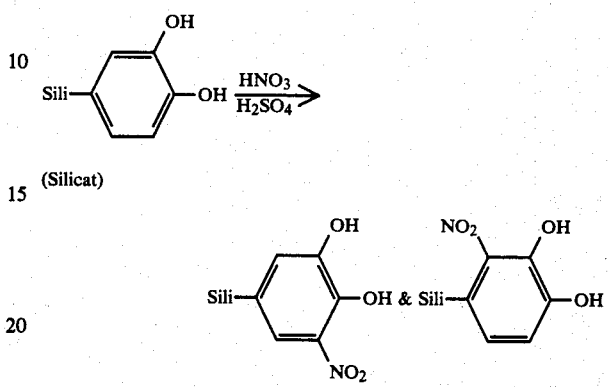

(Silicat)

One batch (prepared from 500 gm. silica) of silicat was cooled in an ice bath thoroughly. To this cooled suspension was added continuously 250 ml. commercial concentrated nitric acid and the mixture was stirred, evacuated and cooled in ice bath for 30 min. Then 250 ml. concentrated sulfuric acid was added very cautiously with careful stirring. The mixture was warmed up considerably and it was cooled in the ice bath. The reaction was allowed to proceed for another two hours. The mixture was then diluted with a large amount of water and then filtered, washed with water, followed by soaking with 5% ammonium hydroxide, giving a mixture reddening in shade and orange filtrates and washings. Thorough washing with water was continued until the washing was colorless. It was then soaked in 5% hydrochloric acid and which brought about a lightening of color from reddish to orange and washed with water again thoroughly. It was stored in this acidified form for subsequent utilization.

EXAMPLE 22

Removal of $UO_2^{2+}$ from Solution Using a Composition Consisting of Desferrioxamine Fixed to a Silica Gel A bed consisting of 4 gms of a composition consisting of desferrioxamine coupled to a silica gel with glutaraldehyde (see example no. 1(e) was placed into a column. The composition was then treated with 100 ml of an aqueous 0.5M sodium dithionite solution to remove any bound metal e.g. iron. The composition was then washed with 100 ml of an aqueous 0.01M sodium acetate solution of pH 5.9 at 20° C. The composition was then contacted at 20° C. with a total of 80 ml of an aqueous solution (pH 6.9) containing Uranyl acetate at a concentration of 600μM the solution being brought into contact with the composition at the rate of 2.3 ml/min. No uranyl ion emerged from the column until a total of 62 ml of the solution had been applied. The composition took up a total of 34.6μ mole of $UO_2^{2+}$ or 8.64μ mole of $UO_2^{2+}$ (2.0 mg of $UO_2^{2+}$) per gram of composition. The loaded composition was thereafter treated with an aqueous 6 mM $Fe^{3+}$ solution (pH 6.9). The composition failed to develop a red colour indicative of the binding of $Fe^{3+}$ thereto; i.e. composition has higher affinity for $UO_2^{2+}$ than for $Fe^{3+}$.

EXAMPLE 23

Removal of $UO_2^{2+}$ from a Citrate Buffered Solution Using a Composition Consisting of Catechol Fixed to a Silica Gel 110 ml. of a buffered uranyl acetate solution (Uranyl acetate 600μM; sodium acetate 60 mM) of pH 6.9 was contacted with 4 gms (dry wgt) of a catechol-glutaraldehyde-silica composition (see example no. 11). The composition was >99.9% efficient in removing Uranyl ion from solution for the first 50 ml of solution contacted with the composition; i.e. the composition took up to 7.3μ mol $UO_2^{2+}$/gm of composition. The efficiency of the composition thereafter progressively decreased. The overall binding capacity of the composition was found to be about 14μM (3.3 mg) $UO_2^{2+}$/gm of composition. Overall the concentration of the Uranyl ion in the solution was lowered to less than 6μM from 600μM.

EXAMPLE 24

Removal of $UO_2^{2+}$ in Trace Amounts from Distilled Water Using a Composition Consisting of Catechol Fixed to a Silica Gel.

42 l. of water containing 285 nM $UO_2^{2+}$ acetate (~pH 6.9) was contacted with 30 gm (dry weight) of a catechol-glutaraldehyde-silica composition (see ex. no. 11) placed in a column, at a rate of 4.5 ml/min; the composition was preconditioned by contact with 100 ml of aqueous 0.1M sodium acetate solution pH 6.9. The loaded composition was then washed with 50 ml aqueous 2N HCl to wash out the $UO_2^{2+}$. It was determined that the amount of $UO_2^{2+}$ removed from the water was such that the 285 nM solution was lowered to <0.2 nM; i.e. an efficiency of >99.9%.

EXAMPLE 25

Removal of $UO_2^{2+}$ from Artificial Sea Water Using a Composition Consisting of Catechol Fixed to a Silica Gel 30 gm (dry weight) of a catechol-glutaraldehyde-silica composition (see ex. No. 11) was placed in a column and contacted with 100 ml of an aqueous 0.1M sodium acetate solution at pH 6.9. 900 ml of 13μM $UO_2^{2+}$ acetate in artificial sea water (forty fathoms) adjusted to pH 6.6 was thereafter contacted with the composition. The composition was then washed with 200 ml of distilled water. The washed composition was then contacted with 100 ml aqueous 2N HCl to wash out the $UO_2^{2+}$. Of the 12μ Mole of $UO_2^{2+}$ in the 900 ml of sea water 11.52 were recovered from the composition that could be eluted with the 2N HCl; (i.e. recovery efficiency of ≈96%).

EXAMPLE 26

Elution of $UO_2^{2+}$ from a Composition Consisting of Catechol Fixed to a Silica Gel to Obtain the $UO_2^{2+}$ in a Concentrated Solution 4 gm (dry wgt) of a catechol-glutaraldehyde-silica composition (see ex no. 11) was loaded with $UO_2^{2+}$ by contact with 50 ml of an aqueous solution (600μM $UO_2$ acetate in 0.1M Na acetate) at pH 6.9. The loaded composition was washed with 100 ml of distilled water and then washed with 50 ml aqueous 2N HCl to wash out the $UO_2^{2+}$. 99.94% of the $UO_2^{2+}$ bound to the composition was removed.

EXAMPLE 27

Removal of $Th^{4+}$ from a Buffered Solution Using a Composition Consisting of Catechol Fixed to a Silica Gel 4 gm (dry weight) of a catechol-glutaraldehyde-silica composition (see ex. no. 11) was placed in a column and treated with 100 ml of an aqueous 0.1M Na acetate solution pH 6.9. The composition was then contacted with 100 ml of an aqueous solution (600μM Th $(NO_3)_4$ in 6 mM Na citrate) pH 6.9 at a rate of 3 ml/min. The results were nearly identical to those in ex. 22.

EXAMPLE 28

Separation of $UO_2^{2+}$ and $Th^{4+}$ Bound to a Composition Consisting of Catechol Fixed to a Silica Gel 30 gms (dry wt) of a catechol-glutaraldehyde-silica composition (see example no. 11) was loaded with $UO_2^{2+}$ and $Th^{4+}$ by contacting it with 100 ml of an aqueous solution containing

| | |
|---|---|
| $Th(NO_3)_4$ | 3 mM |
| $UO_2(acetic)_2$ | 3 mM |
| $Na_3(Citrate)$ | 60 mM |
| pH | 6.9 |

The loaded composition was washed with distilled water and thereafter placed in a column. The composition was then washed with 200 ml of aqueous 60 mM Na Citrate pH 6.9. The composition was then eluted with a continuous pH gradient starting from pH 6.9 and finishing at pH 0.8. The gradient was prepared by starting with an aqueous 0.1M sodium citrate solution of pH 6.9, thereafter mixing said citrate solution with an aqueous 0.3N HCl (the citrate in lower and lower amounts the HCl in higher and higher amounts) until finally finishing with said aqueous 0.3N HCl solution pH 0.8. Over all a total of 150 ml of each solution was used. The $Th^{4+}$ was selectively eluted at a pH of about 4.45. The $UO_2^{2+}$ was eluted at the lower end of the pH gradient.

We claim:

1. A method for inhibiting microbial growth in a liquid nutrient medium containing $Fe^{3+}$ by lowering the $Fe^{3+}$ content thereof to less than 0.1μM characterized in that said medium is contacted with an insoluble siderophoric composition and thereafter said siderophoric composition loaded with $Fe^{3+}$ is separated from said medium, said insoluble siderophoric composition comprising:
    (1) one or more organic siderophoric compounds covalently fixed to the surface of
    (2) a suitable insoluble carrier, said organic siderophoric compounds possessing one or more coordinating sites capable of chelating $Fe^{3+}$.

2. A method as defined in claim 1, wherein said coordinating sites are provided by one or more members of the class consisting of
    (a) a N-substituted hydroxamate group of formula

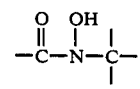

(b) a phenolate group of formula

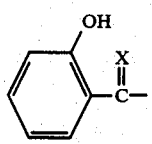

X being an atom of O or N—, and
(c) a catecholate group of formula

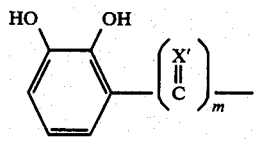

X' being an atom of O or N-and m being 1.

3. A method for inhibiting microbial growth in a liquid nutrient medium containing $Fe^{3+}$ *by lowering the* $Fe^{3+}$ content thereof to less then 0.1μM characterized in that said medium is contacted with an insoluble siderophoric composition and thereafter said siderophoric composition loaded with $Fe^{3+}$ is separated from said medium, said insoluble siderophoric composition comprising
   (1) one or more organic siderophoric compounds covalently fixed to the surface of
   (2) a suitable insoluble carrier, said organic siderophoric compounds possessing one or more coordinating sites capable of chelating $Fe^{3+}$, said organic siderophoric compounds being selected from the class consisting of microbial siderophores.

4. A method as defined in claim 3, wherein said microbial siderophores have a molecular weight of less then 2500 daltons.

5. A method as defined in claim 4, wherein said coordinating sites are provided by one or more members of the class consisting of
   (a) a N-substituted hydroxamate group of formula

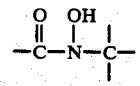

(b) a phenolate group of formula

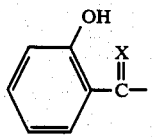

X being an atom of O or N—, and
(c) a catecholate group of formula

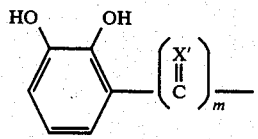

X' being an atom of O or N— and m being 1.

6. A method as defined in claim 3, wherein said microbial siderophores have a molecular weight in the range of 500 to 2500 daltons.

7. A method as defined in claim 6, wherein said coordinating sites are provided by one or more N-substituted hydroxamate groups of formula

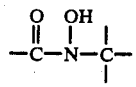

8. A method as defined in claim 6, wherein said coordinating sites are provided by one or more catecholate groups of formula

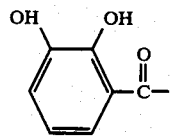

9. A method as defined in claim 6, wherein said coordinating sites are provided by one or more members of the class consisting of
   (a) a N-substituted hydroxamate group of formula

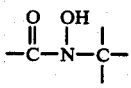

(b) a phenolate group of formula

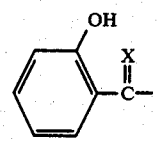

X being an atom of O or N—, and
(c) a catecholate group of formula

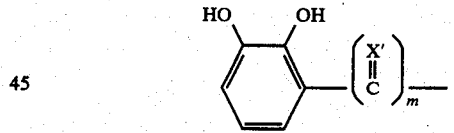

X' being an atom of O or N— and m being 1.

10. A method as defined in claim 3, wherein said coordinating sites are provided by one or more members of the class consisting of
   (a) a N-substituted hydroxamate group of formula

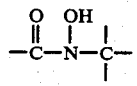

(b) a phenolate group of formula

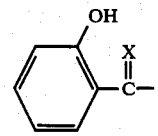

X being an atom of O or N—, and (c) a catecholate group of formula

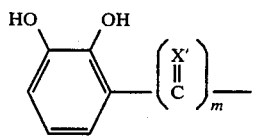

X' being an atom of O or N— and m being 1.

11. A method as defined in claim 3, wherein said organic siderophoric compounds are selected from the class consisting of desferrioxamines.

12. A method as defined in claim 3, wherein the organic siderophoric compound covalently fixed to the carrier is enterobactin.

13. A method for inhibiting microbial growth in a liquid nutrient medium containing $Fe^{3+}$ by lowering the $Fe^{3+}$ content thereof to less then $0.1 \mu M$ characterized in that said medium is contacted with an insoluble siderophoric composition and thereafter said siderophoric composition loaded with $Fe^{3+}$ is separated from said medium, said insoluble siderophoric composition comprising
    (1) one or more catechol compounds covalently fixed to the surface of
    (2) a suitable insoluble carrier, said catechol compounds being covalently fixed to the surface of said carrier at the benzene ring thereof, said catechol compounds being selected from the group consisting of catechol substituted on the benzene ring by one or two electrophilic substituents.

14. A method as defined in claim 13, wherein the catechol compound covalently fixed to the carrier is unsubstituted catechol.

15. A method as defined in claim 13, wherein said catechol compounds are selected from the group consisting of catechol substituted on the benzene ring by one or two substituents selected from the class consisting of halogen atoms, NO and $NO_2$.

16. A method as defined in claim 13, wherein said catechol compounds are selected from the group consisting of catechol substituted on the benzene ring by one or two halogen atoms.

17. A method as defined in claim 16, wherein said halogen atoms are selected from chlorine and bromine.

18. A method as defined in claim 13, wherein said catechol compound is selected from the group consisting of catechol monosubstituted on the benzene ring by a substituent selected from NO and $NO_2$.

19. A method for removing $Fe^{3+}$, $Th^{4+}$, $UO_2^{2+}$ or mixtures thereof from solution characterized in that the solution is contacted with an insoluble composition comprising a member selected from the class consisting of
    (A) an insoluble composition comprising
        (1) one or more organic chelating compounds, covalently fixed to the surface of
        (2) a suitable insoluble carrier, said organic chelating compounds possessing one or more coordinating sites, said organic chelating compounds being selected from the class consisting of microbial siderophores and
    (B) an insoluble composition comprising
        (1) one or more catechol compounds covalently fixed to the surface of
        (2) a suitable insoluble carrier, said catechol compounds being covalently fixed to the surface of said carrier at the benzene ring thereof, said catechol compounds being selected from the group consisting of unsubstituted catechol and catechol substituted on the benzene ring by one or two electrophilic substituents.

20. A method for removing $Fe^{3+}$, $Th^{4+}$, $UO_2^{2+}$ or mixtures thereof from solution characterized in that the solution is contacted with an insoluble composition comprising
    (1) one or more organic chelating compounds, covalently fixed to the surface of
    (2) a suitable insoluble carrier, said organic chelating compounds possessing one or more coordinating sites, said organic chelating compounds being selected from the class consisting of microbial siderophores.

21. A method as defined in claim 20, wherein said microbial siderophores have a molecular weight of less than 2500 daltons.

22. A method as defined in claim 21, wherein said coordinating sites are provided by one or more members of the class consisting of
    (a) a N-substituted hydroxamate group of formula

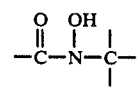

(b) a phenolate group of formula

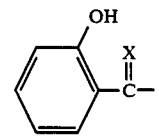

X being an atom of O or N—, and
    (c) a catecholate group of formula

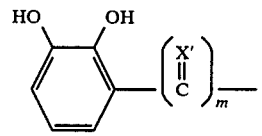

X' being an atom of O or N— and m being 1.

23. A method as defined in claim 20, wherein said microbial siderophores have a molecular weight in the range of 500 to 2500 daltons.

24. A method as defined in claim 23, wherein said coordinating sites are provided by one or more N-substituted hydroxamate groups of formula

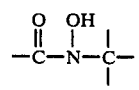

25. A method as defined in claim 23, wherein said coordinating sites are provided by one or more catecholate groups of formula

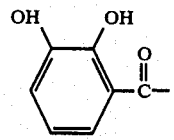

26. A method as defined in claim 23, wherein said coordinating sites are provided by one or more members of the class consisting of (a) a N-substituted hydroxamate group of formula

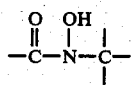

(b) a phenolate group of formula

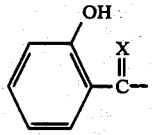

X being an atom of O or N—, and (c) a catecholate group of formula

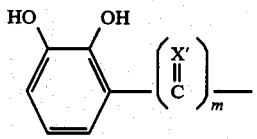

X' being an atom of O or N— and m being 1.

27. A method as defined in claim 20, wherein said coordinating sites are provided by one or more members of the class consisting of (a) a N-substituted hydroxamate group of formula

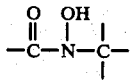

(b) a phenolate group of formula

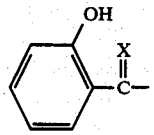

X being an atom of O or N—, and (c) a catecholate group of formula

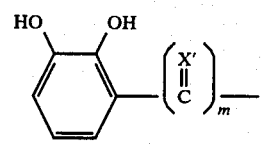

X' being an atom of O or N— and m being 1.

28. A method as defined in claim 20, wherein said organic chelating compounds are selected from the class consisting of desferrioxamines.

29. A method as defined in claim 20, wherein the organic chelating compound covalently fixed to the carrier is enterobactin.

30. A method for removing $Fe^{3+}$, $Th^{4+}$, $UO_2^{2+}$ or mixtures thereof from solution characterized in that the solution is contacted with an insoluble composition comprising:
(1) one or more catechol compounds covalently fixed to the surface of
(2) a suitable insoluble carrier, said catechol compounds being covalently fixed to the surface of said carrier at the benzene ring thereof, said catechol compounds being selected from the group consisting of unsubstituted catechol and catechol substituted on the benzene ring by one or two electrophilic substituents.

31. A method as defined in claim 30, wherein the catechol compound fixed to the carrier is unsubstituted catechol.

32. A method as defined in claim 30, wherein said catechol compounds are selected from the group consisting of catechol substituted on the benzene ring by one or two substituents selected from the class consisting of halogen atoms, NO and $NO_2$.

33. A method as defined in claim 30, wherein said catechol compounds are selected from the group consisting of catechol substituted on the benzene ring by one or two halogen atoms.

34. A method as defined in claim 33, wherein said halogen atoms are selected from chlorine and bromine.

35. A method as defined in claim 30, wherein said catechol compound is selected from the group consisting of catechol monosubstituted on the benzene ring by a substituent selected from NO and $NO_2$.

36. A method as defined in claim 30, wherein said catechol compounds convalently fixed to the carrier are selected from the group consisting of catechol substituted on the benzene ring by one or two electrophilic substituents.

37. A method as defined in claim 36, wherein said electrophilic substituents are selected from the group consisting of halogen atoms, NO, $NO_2$, COOH and

38. A method for removing $Th^{4+}$ from solution comprising the step of contacting a solution which contains $Th^{4+}$ with an insoluble composition comprising catechol convalently fixed to the surface of a suitable insoluble carrier, said catechol being fixed at the benzene ring thereof to the surface of said carrier.

* * * * *